US008148320B2

(12) United States Patent
Kotula et al.

(10) Patent No.: US 8,148,320 B2
(45) Date of Patent: Apr. 3, 2012

(54) PEPTIDE INHIBITORS OF ABL KINASES

(75) Inventors: Leszek Kotula, Marlboro, NJ (US); Xiaoling Xiong, Fresh Meadows, NY (US)

(73) Assignee: New York Blood Center, Inc., New York, NY (US)

( * ) Notice: Subject to any disclaimer, the term of this patent is extended or adjusted under 35 U.S.C. 154(b) by 738 days.

(21) Appl. No.: 12/095,728

(22) PCT Filed: Nov. 29, 2006

(86) PCT No.: PCT/US2006/045570
§ 371 (c)(1),
(2), (4) Date: Jun. 2, 2008

(87) PCT Pub. No.: WO2007/064647
PCT Pub. Date: Jun. 7, 2007

(65) Prior Publication Data
US 2010/0184652 A1    Jul. 22, 2010

Related U.S. Application Data

(60) Provisional application No. 60/741,208, filed on Dec. 1, 2005.

(51) Int. Cl.
*A61K 38/16* (2006.01)
*A61K 38/10* (2006.01)
*C07K 7/08* (2006.01)
*C07K 14/00* (2006.01)
*A61P 35/00* (2006.01)

(52) U.S. Cl. ...... 514/1.1; 514/19.3; 514/19.5; 514/19.6; 514/21.4; 514/21.5; 530/324; 530/327; 530/350

(58) Field of Classification Search .................. None
See application file for complete search history.

(56) References Cited

U.S. PATENT DOCUMENTS

| | | | |
|---|---|---|---|
| 5,595,756 A * | 1/1997 | Bally et al. ................ | 424/450 |
| 6,255,074 B1 | 7/2001 | Pendergast et al. | |
| 6,812,339 B1 | 11/2004 | Venter et al. | |
| 2003/0109690 A1 * | 6/2003 | Ruben et al. .............. | 536/23.1 |
| 2005/0003450 A1 | 1/2005 | Rush et al. | |
| 2005/0065081 A1 | 3/2005 | Dorey et al. | |
| 2005/0181375 A1 | 8/2005 | Aziz et al. | |

FOREIGN PATENT DOCUMENTS

| WO | 00/77040 A2 | 12/2000 |
|---|---|---|
| WO | 2006/086111 A | 8/2006 |

OTHER PUBLICATIONS

Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
SEQ ID No. 4382 from US 2003/0109690.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Adrian, F. et al. "Allosteric Inhibitors of Bcr-abl-dependent cell proliferation", Nat Chem Biol, vol. 2, pp. 95-102, 2006.
Al-Ali, H. et al. "High Incidence of BCR-ABL Kinase Domain Mutations and Absence of Mutations of the PDGFR and KIT Activation Loops in CML Patients with Secondary Resistance to imatinib", Hematol J, vol. 5, pp. 55-60, 2004.
Azam, M. et al. "Mechanisms of Autoinhibition and STI-571/imatinib Resistance Revealed by Mutagenesis of BCR-ABL", Cell, vol. 112, pp. 831-843, 2003. Biesova, Z. et al. "Isolation and characterization of e3B1, an eps8 binding protein that regulates cell growth", Oncogene, vol. 14, pp. 233-241, 1997.
Brasher, BB. et al. "Mutational analysis of the regulatory function of the c-Abl Src homology 3 domain", Oncogene, vol. 20, pp. 7744-7752, 2001.
Brasher, BB. et al. "c-Abl has High Intrinsic Tyrosine Kinase activity that is Stimulated by Mutation of the Src Homology 3 Domain and by Autophosphorylation at Two Distinct Regulatory Tyrosines", J. Biol Chem, vol. 275, pp. 35631-35637, 2000.
Buchdunger, E., et al. "Inhibition of the Abl protein-tyrosine Kinase In Vitro and In Vivo by a 2-phenylaminopyrimidine derivative", Cancer Res, vol. 56, pp. 100-104, 1996.

(Continued)

*Primary Examiner* — Julie Ha
(74) *Attorney, Agent, or Firm* — K&L Gates LLP; Louis C. Cullman; Michelle Glasky Bergman

(57) ABSTRACT

Provided are purified compounds comprising SEQ ID NO:1, where the tyrosine at residue (10) is phosphorylated. Also provided are purified compounds comprising SEQ ID NO:1, where the amino acid sequence of the compound is less than 400 amino acids. Additionally provided are methods of determining whether an agent is a candidate inhibitor of an Abl kinase. Further provided are methods of inhibiting an Abl kinase. Also provided are methods of treating a patient having a condition characterized by a mutant Abl kinase. Additionally provided are methods of treating a patient at risk for a condition characterized by a mutant Abl kinase. Methods of labeling an Abl kinase are also provided. Additionally, methods of isolating an Abl kinase from a tissue are provided.

2 Claims, 17 Drawing Sheets

OTHER PUBLICATIONS

Courtneidge, S.A. "Cancer: Escape from Inhibition", Nature, vol. 422, pp. 827-828, 2003.

Cowan-Jacob, S.W., et al. "The Crystal Structure of a c-Src Complex in an Active Conformation Suggests Possible Steps in c-Src Activation", Structure (Camb), vol. 13, pp. 861-871, 2005.

Dai, Z. et al. "Abi-2, a novel SH3-containing protein interacts with the c-Abl tyrosine kinase and modulates c-Abl transforming activity", Genes Dev, vol. 9, pp. 2569-2582, 1995.

Dambosky, J., et al. "TRITON: graphic software for rational engineering of enzymes", Trends Biochem Sci, vol. 26, pp. 71-73, 2001.

Druker, B.J., et al. "Chronic myelogenous leukemia", Hematology (Am Soc Hematol Educ Program), pp. 87-112, 2001a.

Druker, B.J. et al. "Efficacy and safety of a specific inhibitor of the BCR-ABL tyrosine kinase in chronic myeloid leukemia", N Eng J Med, vol. 344, pp. 1031-1037, 2001b.

Druker, B.J. et al. "Effects of a selective inhibitor of the Abl tyrosine kinase on the growth of Bcr-Abl positive cells", Nat Med, vol. 2, pp. 561-566, 1996.

Fiser, A. et al. "Modeller: generation and refinement of homology-based protein structure models", Methods Enzymol, vol. 374, pp. 461-491, 2003.

Garber, K. "The second wave in kinase cancer drugs", Nat Biotechnol, vol. 24, pp. 127-130, 2006.

Goldman, J.M. "Chronic myeloid leukemia-advances in biology and new approaches to treatment", N Engl J Med, vol. 349, pp. 1451-1464, 2003.

Gorre, M.E., et al. "Clinical resistance to STI-571 cancer therapy caused by BCR-ABL gene mutation or amplification", Science, vol. 293, pp. 876-880, 2001.

Goss, V.L. et al. "A common phosphotyrosine signature for the Bcr-Abl kinase", Blood, vol. 107, pp. 4888-4897, 2006.

Hantschel, O. et al. "A myristoyl/phosphotyrosine switch regulates c-Abl", Cell, vol. 112, pp. 845-857, 2003.

Hantschel, O. et al. "Regulation of the c-Abl and Bcr-Abl tyrosine kinases", Nat Rev Mol Cell Biol, vol. 5, pp. 33-44, 2004.

Ikeguchi A., et al. "Inhibition of v-Abl transformation in 3T3 cells overexpressing different forms of the Abelson interactor protein Abi-1" Oncogene, vol. 20, pp. 4926-4934, 2001.

Jackson, P. et al. "N-terminal mutations activate the leukomogenic potential of the myristoylated form of c-abl", Embo J, vol. 8, pp. 449-456, 1989.

Khorashad, J.S. et al. "The presence of a BCR-ABL mutant allele in CML does not always explain clinical resistance to imatinib", Leukemia, 2006.

Koleske, A.J., et al. "Essential roles for the Abl and Arg tyrosine kinases in neurulation", Neuron, vol. 21, pp. 1259-1272, 1998.

Leng, Y., et al. "Abelson-interactor-1 promotes WAVE2 membrane translocation and Abelson-mediated tyrosine phosphorylation required for WAVE2 activation", Proc Natl Acad Sci USA, vol. 102, pp. 1098-1103, 2005.

Lewis, J.M., et al. "Integrin regulation of c-Abl tyrosine kinase activity and cytoplasmic-nuclear transport", Proc Natl Acad Sci USA, vol. 93, pp. 15174-15179, 1996.

Macoska, J.A., et al. "Loss of expression of human spectrin src homology domain binding protein 1 is associated with 10p loss in human prostatic adenocarcinoma", Neoplasia, vol. 3, pp. 99-104, 2001.

Maruoka, M., et al. "Identification of B cell adaptor for PI3-kinase (BCAP) as an Abl interactor 1-regulated substrate of Abl kinases", FEBS Lett, vol. 579, pp. 2986-2990, 2005.

Mayer, B.J., et al. "Point mutations in the abl SH2 domain coordinately impair phosphotyrosine binding in vitro and transforming activity in vitro", Mol Cell Biol, vol. 12, pp. 609-618, 1992.

Miething, C., et al. "The Bcr-Abl mutations T315I and Y253H do not confer a growth advantage in the absence of imatinib", Leukemia, 2006.

Nagar, B., et al. "Organization of the SH3-SH2 unit in active and inactive forms of the c-Abl tyrosine kinase", Mol Cell, vol. 21, pp. 787-798, 2006.

Nagar, B., et al. "Structural basis for the autoinhibition of c-Abl tyrosine kinase", Cell, vol. 12, pp. 859-871, 2003.

O'Hare, T., et al. "AMN107: tightening the grip of imatinib", Cancer Cell, vol. 7, pp. 117-119, 2005.

Pluk, H., et al. "Autoinhibition of c-Abl", Cell, vol. 108, pp. 247-259, 2002.

Schindler, T., et al. "Structural mechanism for STI-571 inhibition of abelson tyrosine kinase", Science, vol. 289, pp. 1938-1942, 2000.

Shah, N.P. et al. Overriding imatinib resistance with a novel ABL kinese inhibitor. Science, vol. 305, pp. 399-401, 2004.

Shi, Y., et al. "Abl-interactor-1, a novel SH3 protein binding to the carboxy-terminal portion of the Abl protein, suppresses v-abl transforming activity", Genes Dev, vol. 9, pp. 2583-2597, 1995.

Songyang, Z., et al. "Catalytic specificity of protein-tyrosine kinases is critical for selective signalling", Nature, vol. 373, pp. 536-539, 1995.

Stuart, J.R., et al. "c-Abl interacts with the WAVE2 signaling complex to induce membrane ruffling and cell spreading", J Biol Chem, vol. 281, pp. 31290-31297, 2006.

Tani, K et al. "Abl interactor 1 promotes tyrosine 296 phosphorylation of mammalian enabled (Mena) by c-Abl kinase", J Biol Chem, vol. 278, pp. 21685-21692, 2003.

Tanis, K. et al. "Two distinct phosphorylation pathways have additive effects on Abl family kinase activation", Mol Cell Biol, vol. 23, pp. 3884-3896, 2003.

Thomas, S.M., et al. "Cellular functions regulated by Src family kinases", Annu Rev Cell Dev Biol, vol. 13, pp. 513-609, 1997.

Von Bubnoff, N., et al. "BCR-ABL gene mutations in relation to clinical resistance of Philadelphia-chromosome-positive leukemia to STI571: a prospective study", Lancet, vol. 359, pp. 487-491, 2002.

Wang, J.Y. "Controlling Abl: auto-inhibition and co-inhibition?", Nat Cell Biol, vol. 6, pp. 3-7, 2004.

Weisberg, E., et al. "Characterization of AMN107, a selective inhibitor of native and mutant Bcr-Abl", Cancer Cell, vol. 7, pp. 129-141, 2005.

Williams, J.C., et al. "The 2.35 A crystal structure of the inactivated form of chicken Src: a dynamic molecule with multiple regulatory interactions", J Mol Biol, vol. 274, pp. 757-775, 1997.

Woodring, P.J., et al. "Regulation of F-actin-dependent processes by the Abl family of tyrosine kinases", J Cell Sci, vol. 116, pp. 2613-2626, 2003.

Woodring, P.J., et al. "Modulation of the F-actin cytoskeleton by c-Abl tyrosine kinase in cell spreading and neurite extension", J Cell Biol, vol. 156, pp. 879-892, 2002.

Xu, J., et al. "Human spectrin Src homology 3 domain binding protein 1 regulates macropinocytosis in NIH 3T3 cells", J Cell Sci, vol. 113, Pt 21, pp. 3805-3814, 2000.

Xu, W., et al. "Crystal structures of c-Src reveal features of its autoinhibitory mechanism", Mol Cell, vol. 3, pp. 626-639, 1999.

Ziemnicka-Kotula, D., et al. "Identification of a candidate human spectrin Src homology 3 domain-binding protein suggests a general mechanism of association of tyrosine kinases with the spectrin-based membrane skeleton", J Biol Chem, vol. 273, pp. 13681-13692, 1998.

Kotula L. et al. The role of human spectrin SH3 domain binding protein 1 (HSSH3BP1) in prostatic carcinoma. Sep. 2004. http://www.dtic.mil/cgi-bin/GetTRDoc?AD=ADA430579&Location=U2&doc=GetTRDoc.pdf.

Kotula L. et al. The role of human spectrin SH3 domain binding protein 1 (HSSH3BP1) in prostatic carcinoma. Sep. 2003. http://www.dtic.mil/cgi-bin/GetTRDoc?AD=ADA419543&Location=U2&doc=GetTRDoc.pdf.

Kotula L. et al. "Phosphorylation of Abi-1/Hssh3bp1 by c-Abl tyrosine kinase in vitro and in NIH 3T3 cells." Molecular Biology of the Cell. 15:supplement, p. 413A, 2004.

* cited by examiner

FIG. 2 (A-B)
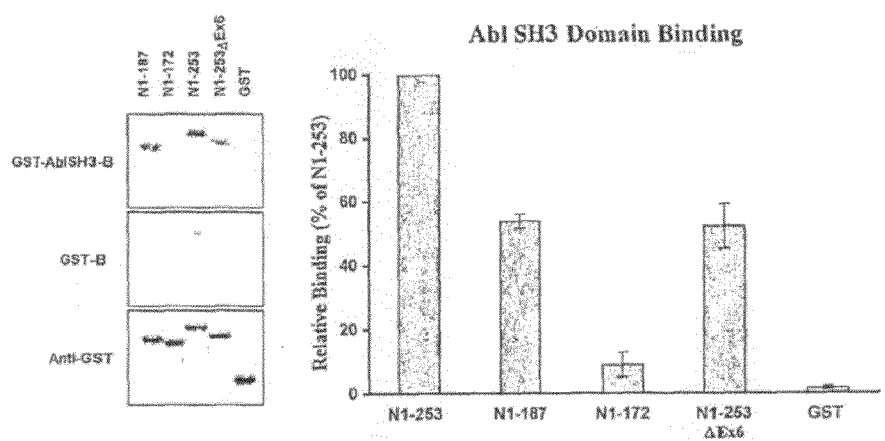
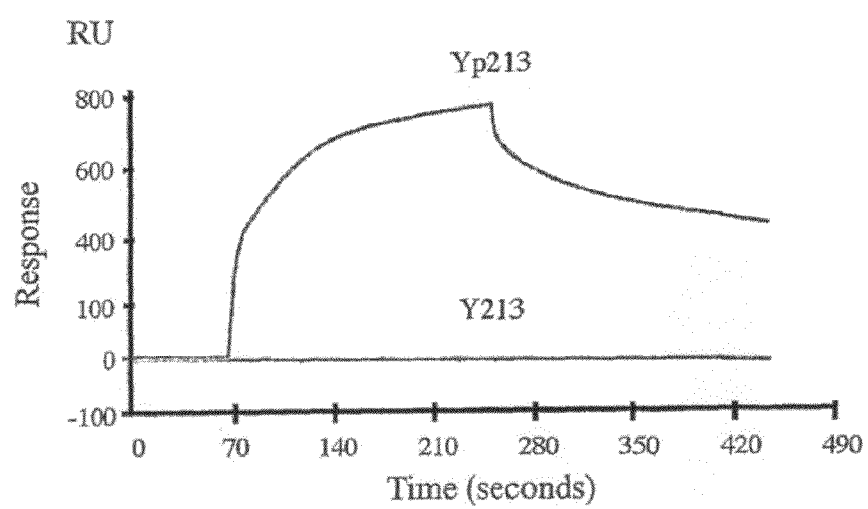

FIG. 2 (C-D)
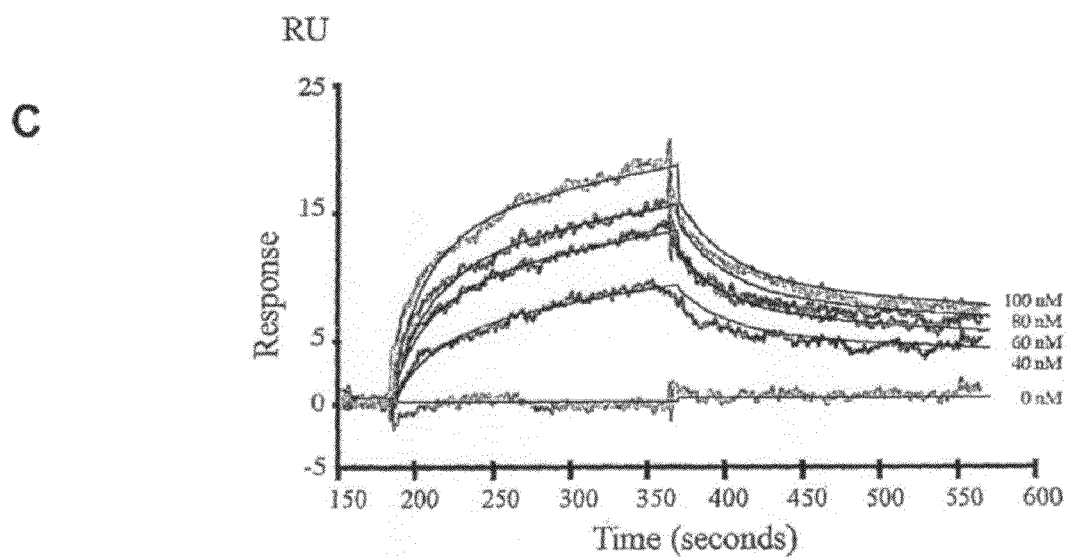
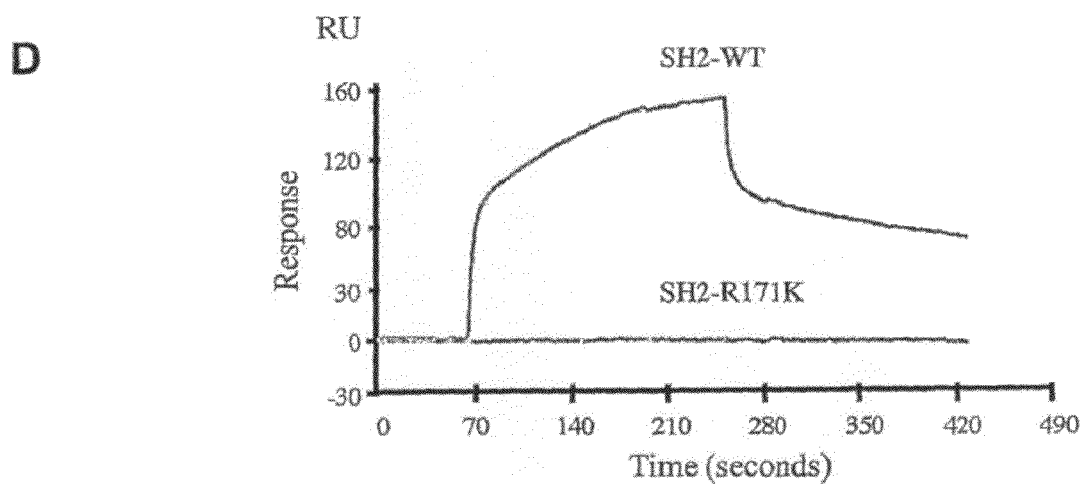

FIG. 3 (A-B)
A
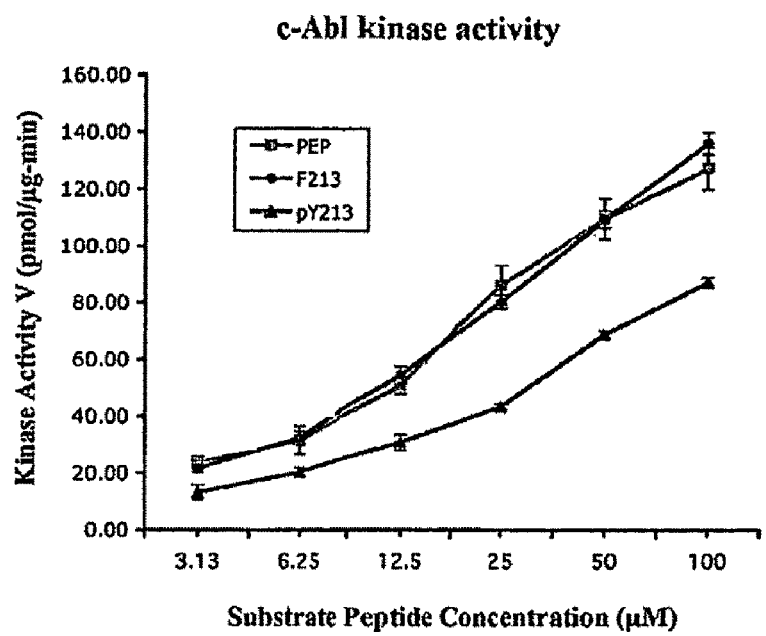
B
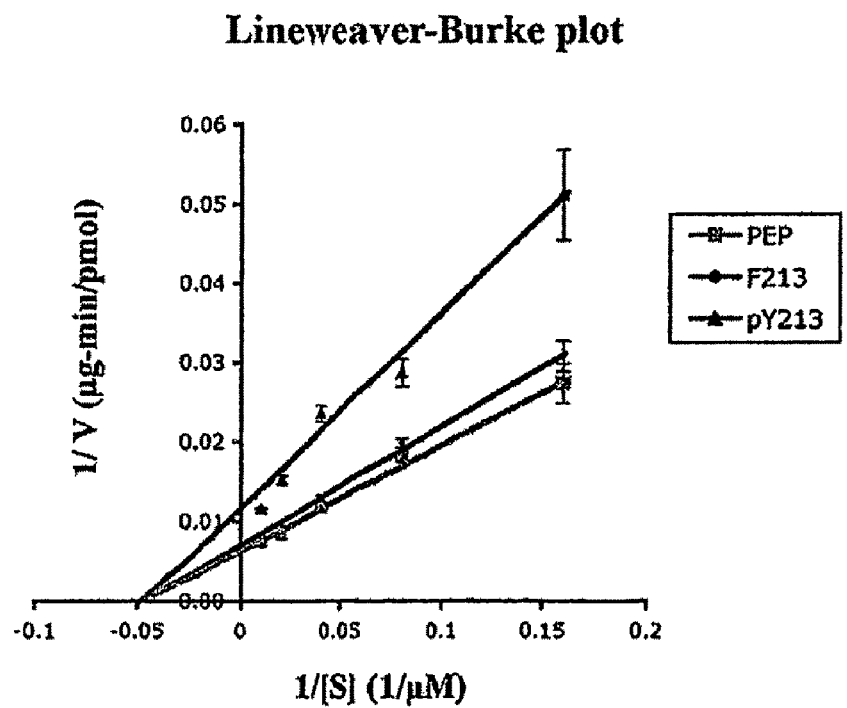

FIG. 3 (C-D)
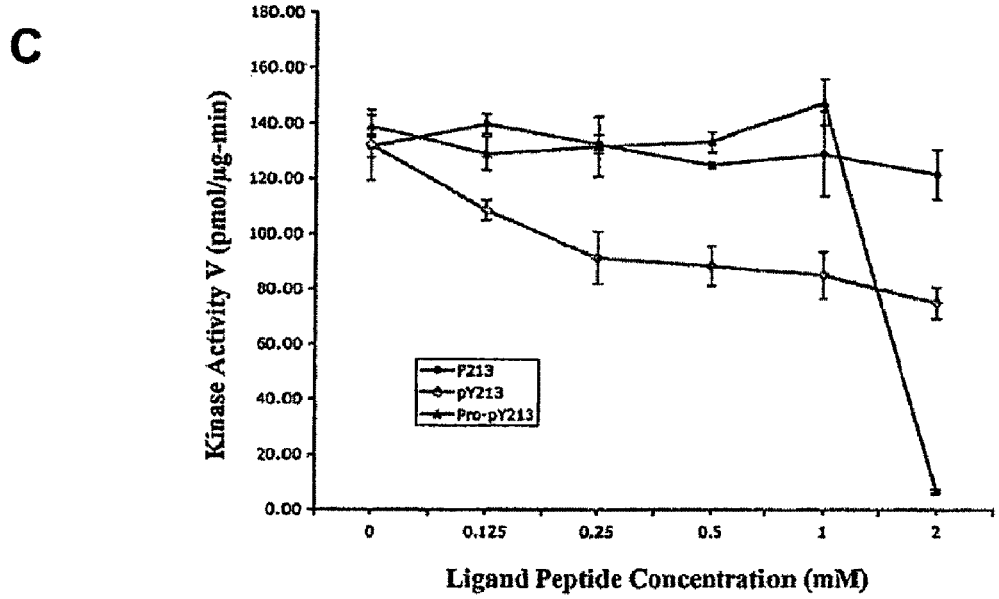
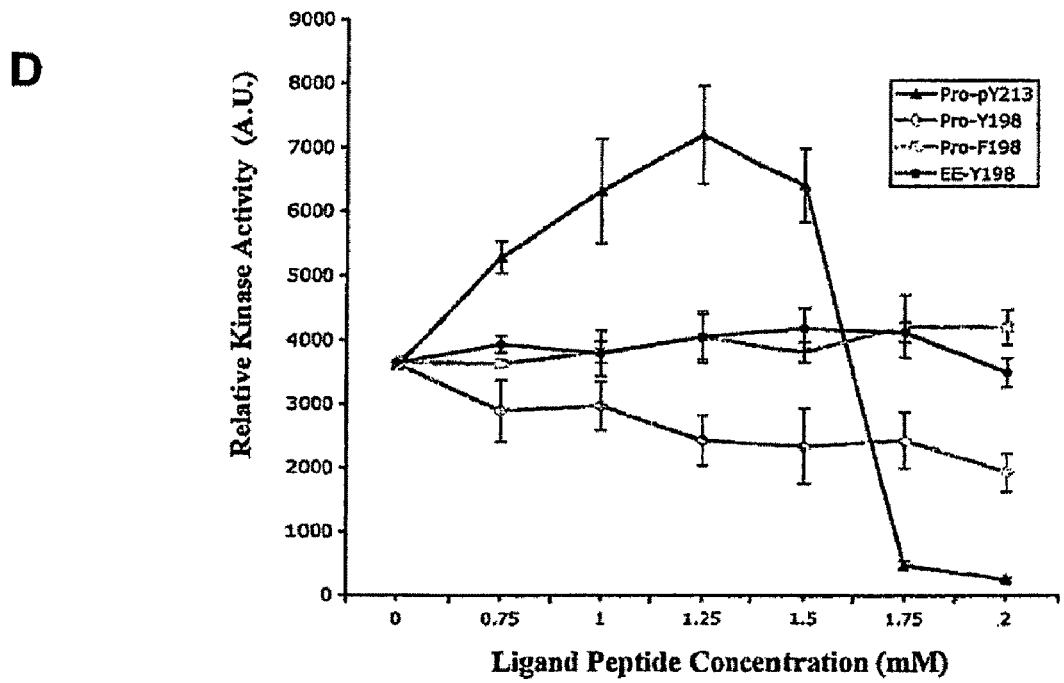

FIG. 3 (E-F)
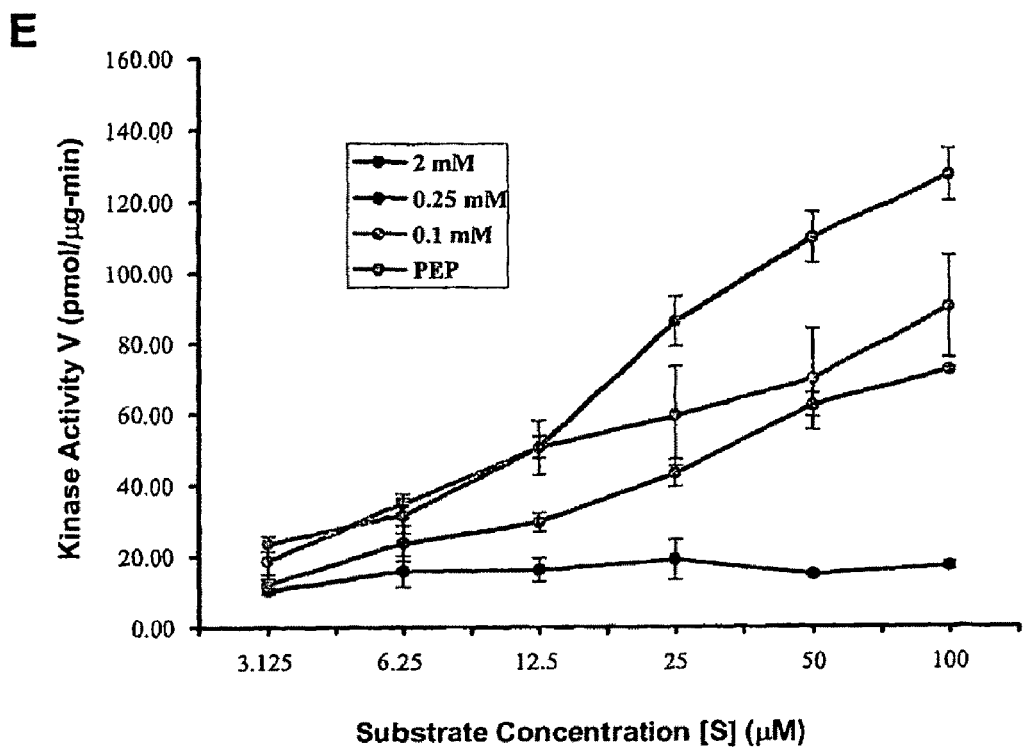
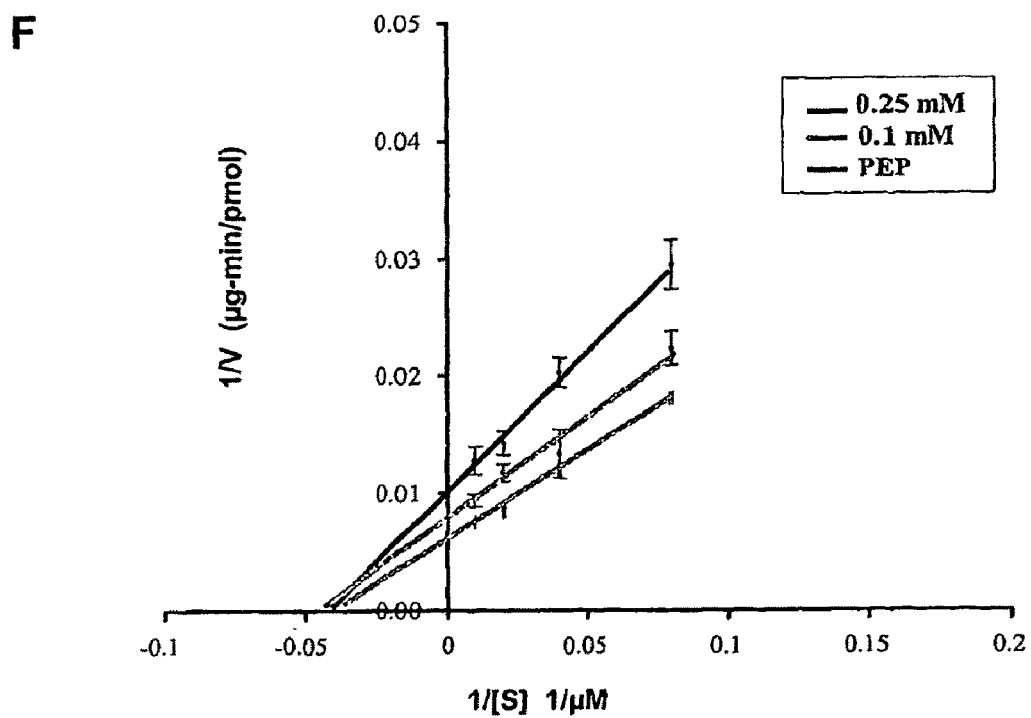

FIG. 4
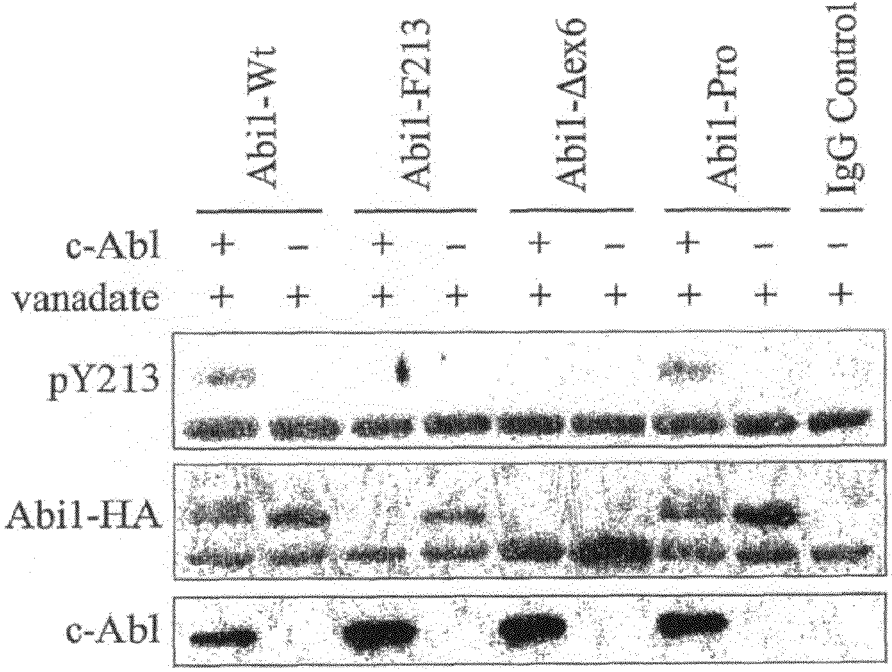
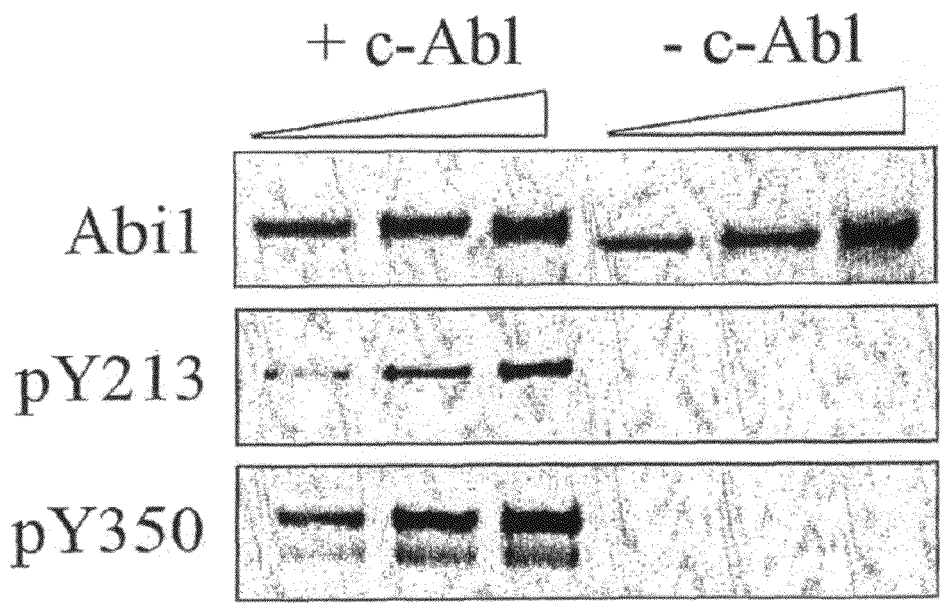

FIG. 5 (B-C)
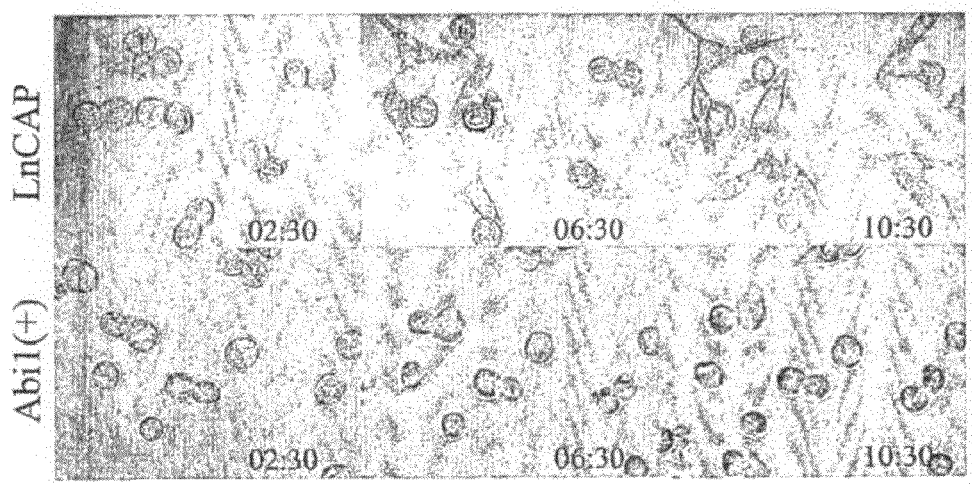
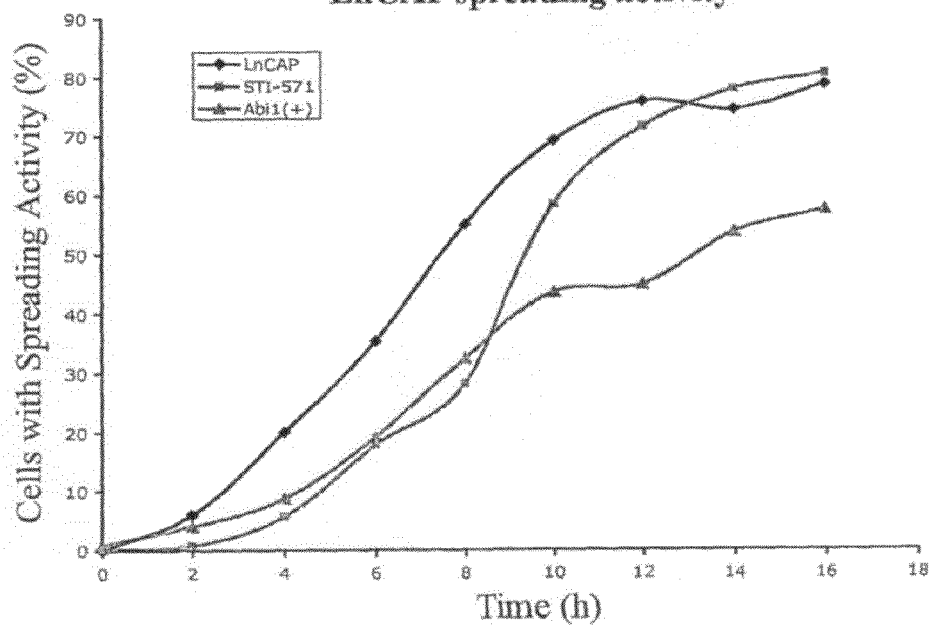

FIG. 6 (A-B)
A
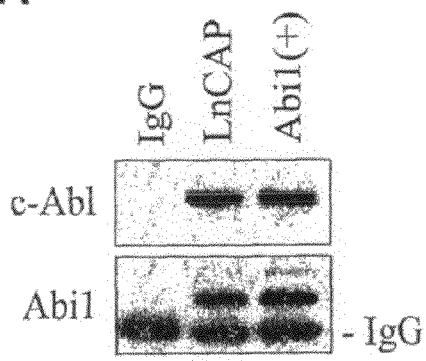 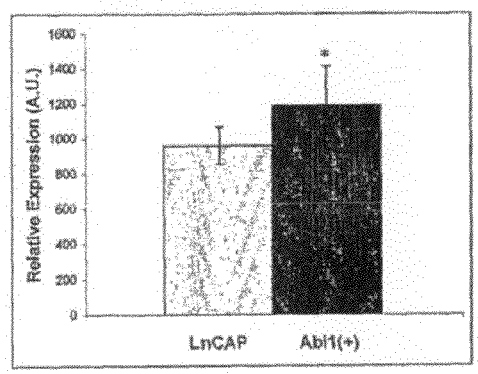
B
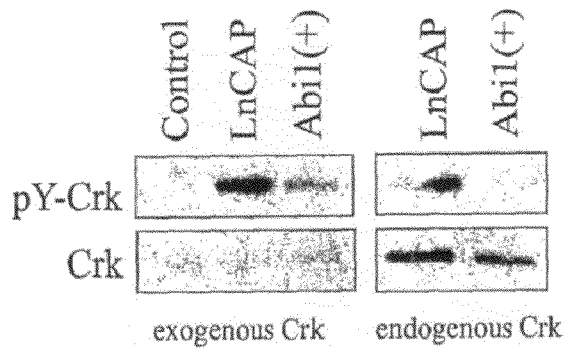 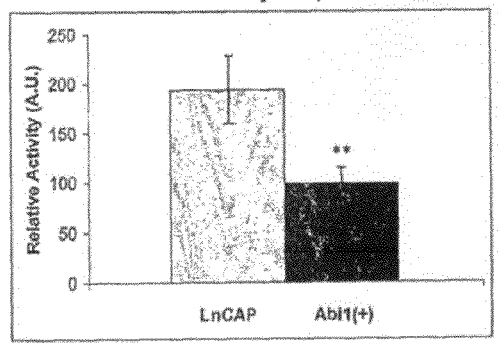

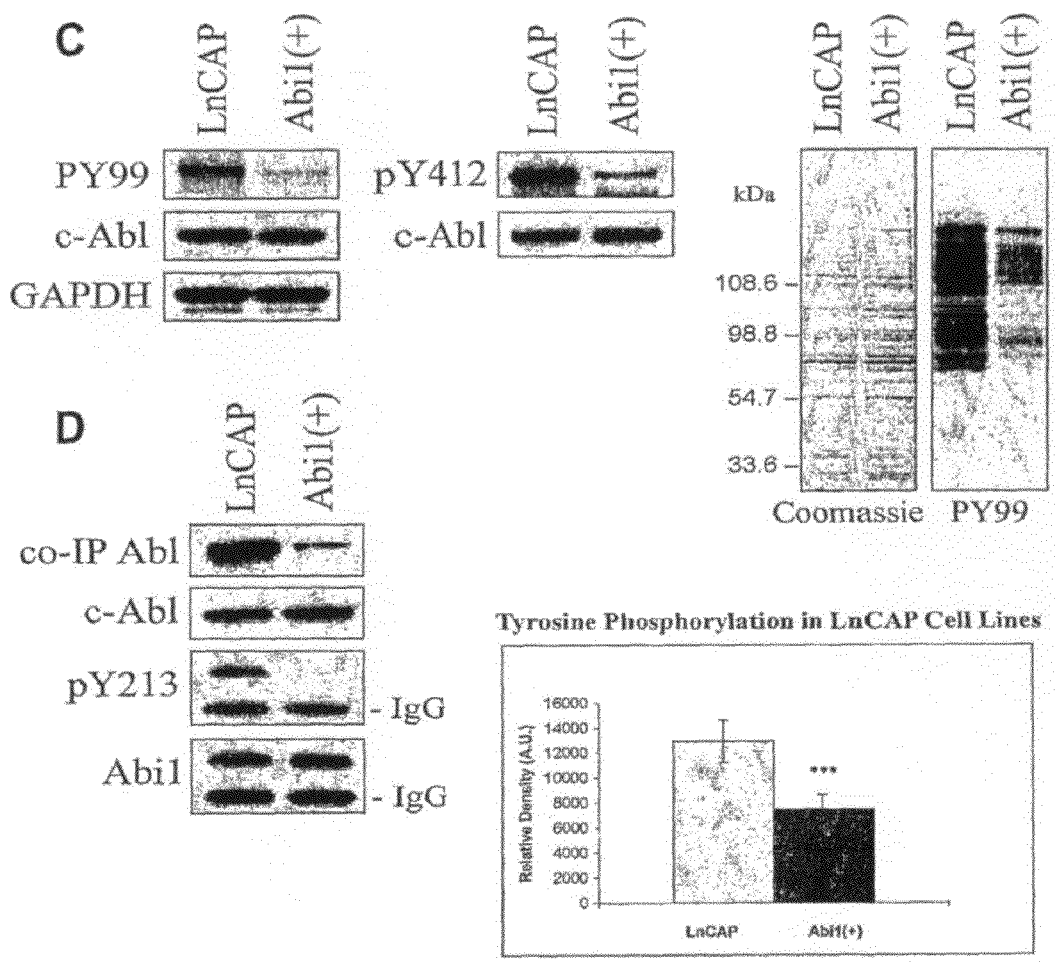
FIG. 6 (C-D)

FIG. 7 (A-B)
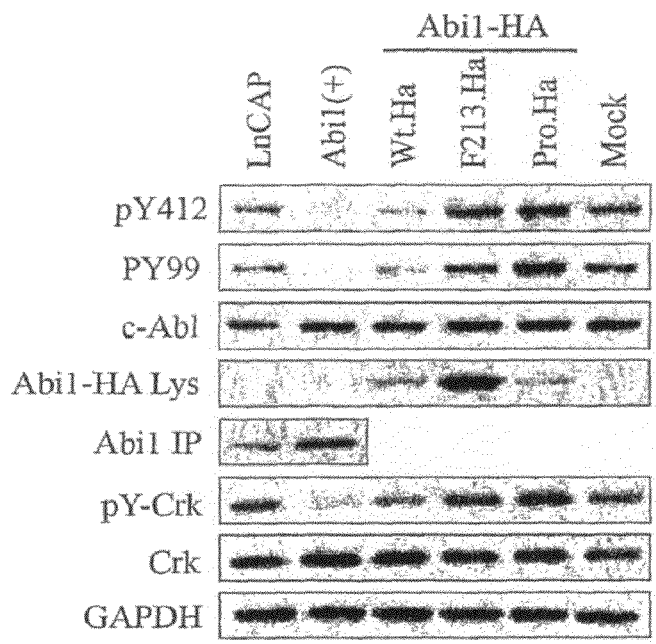
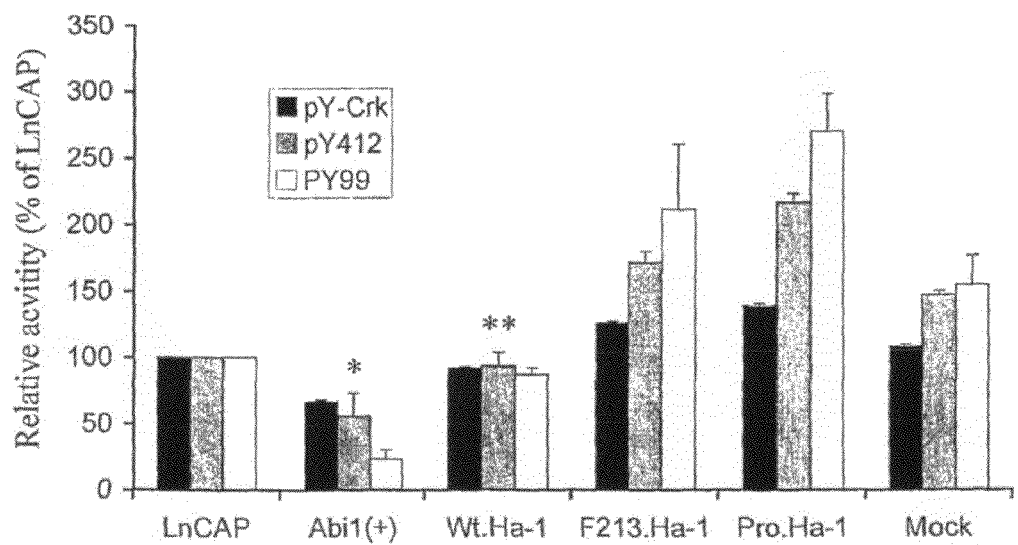

FIG. 7 (C-D)
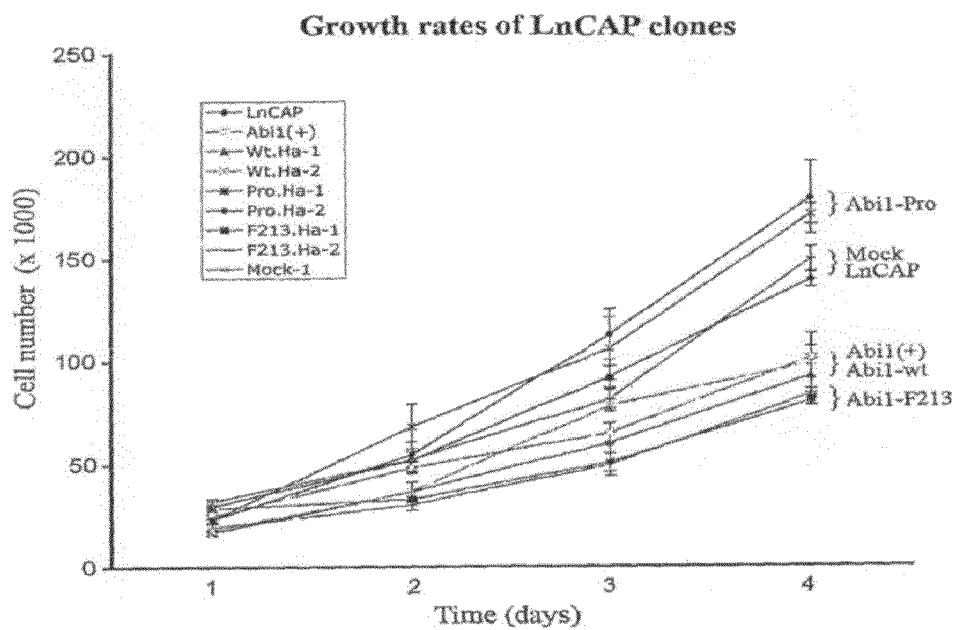
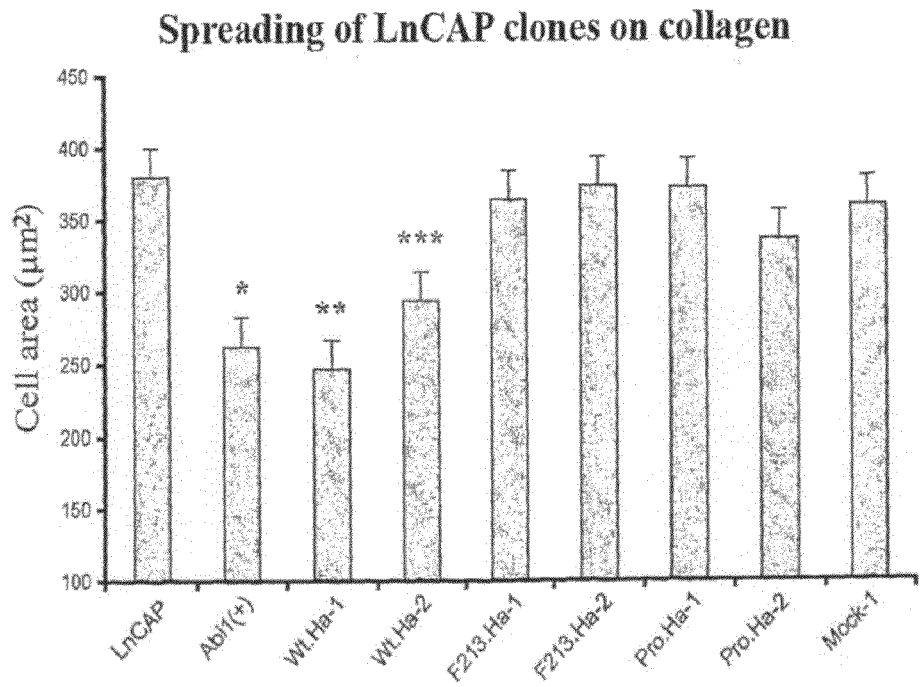

FIG. 8
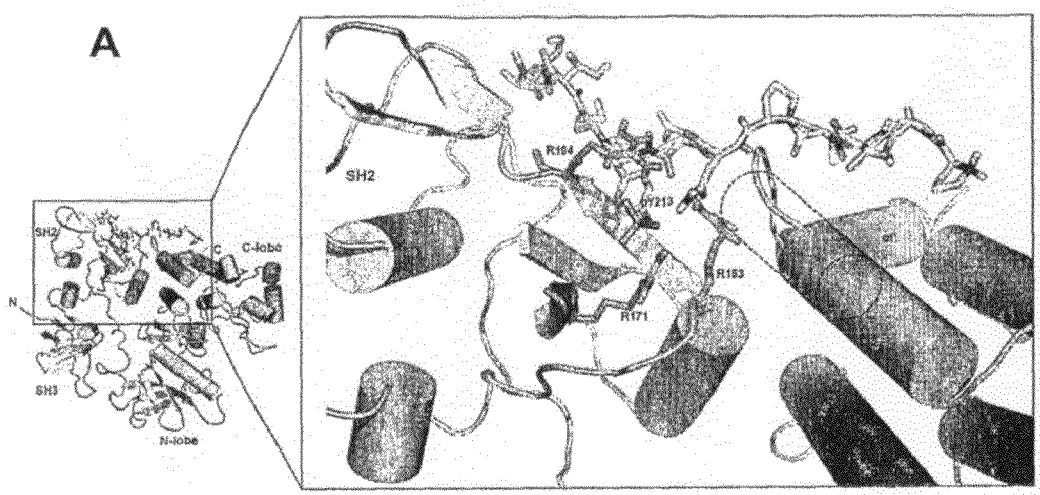
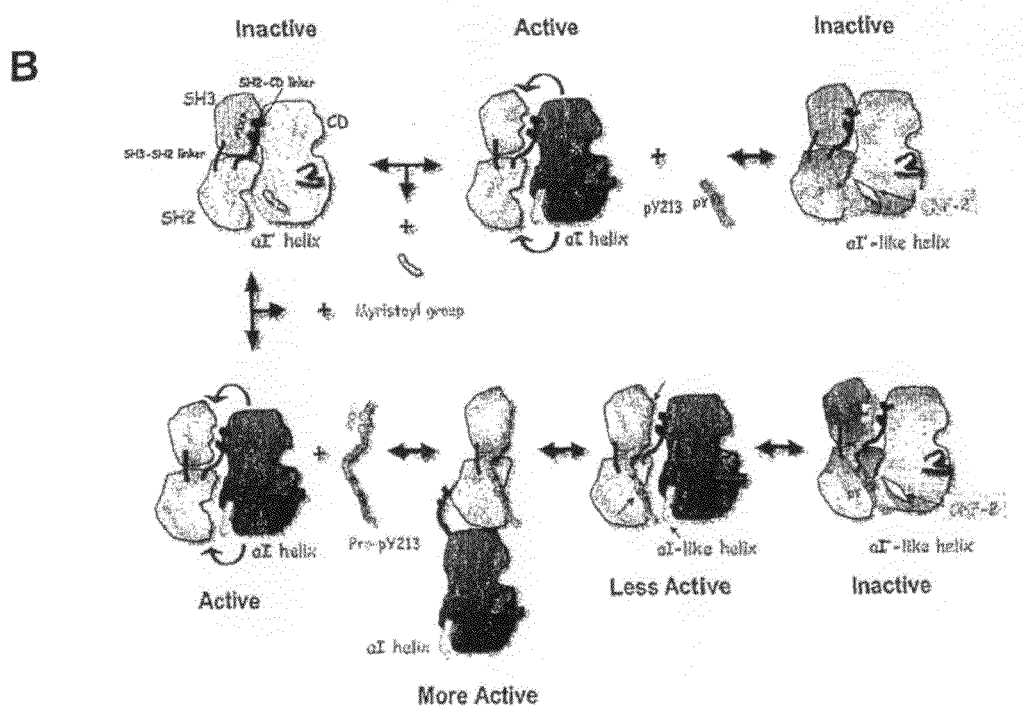

PEPTIDE INHIBITORS OF ABL KINASES

CROSS-REFERENCE TO RELATED APPLICATION

This application claims the benefit of U.S. Provisional Application No. 60/741,208 filed Dec. 1, 2005.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant DAMD17-01-1-0096 awarded by The Department of Defense and Grant R01 NS44968 from The National Institute of Neurological Disorders and Stroke.

BACKGROUND OF THE INVENTION (1) Field of the Invention

The present invention generally relates to regulation of kinase activity. More specifically, the invention is directed to inhibitors of AbI kinases.

(2) Description of the Related Art

Nonreceptor tyrosine kinases are major regulators of cell signaling downstream of extracellular stimuli. The ubiquitous nonreceptor tyrosine kinase c-AbI tyrosine kinase has been implicated in cell proliferation, apoptosis downstream of growth factors, integrin, and cytokine signaling (Woodring et al., 2003). The critical role of c-AbI kinase in cell proliferation is illustrated by the manifestation of chronic myelogenous leukemia (CML) due to expression of BCR-AbI, a kinase-activated mutant form of c-AbI (Goldman and Melo, 2003). However, it is not clear how BCR-AbI or c-AbI kinase activity is regulated in cells.

Auto-inhibition has emerged as the major mechanism of regulation of nonreceptor tyrosine kinases such as c-Src and c-AbI (Courtneidge, 2003; Hantschel et al., 2003; Nagar et al., 2003; Thomas and Brugge, 1997; Wang, 2004). These kinases share high structural homology conferred by the presence of highly conserved structural domains: SH3, SH2, and the catalytic domain. Crystal structures of c-Src (Williams et al., 1997; Xu et al., 1999) and c-AbI (Hantschel et al., 2003; Nagar et al., 2003) reveal that their SH3 and SH2 domains bind to the catalytic domain and induce an autoinhibitory conformation, providing the basic mechanism of regulation of these kinases. Additional regulation of c-Src and c-AbI is, however, provided by nonhomologous sequences of these kinases imposing additional inhibitory constraints. In c-Src this inhibition is achieved by intramolecular interaction of the SH2 domain with the phosphorylated tyrosine 527 located in C-terminus on the same molecule (Thomas and Brugge, 1997). In c-AbI there is no internal phosphotyrosine-SH2 domain interaction, precluding this inhibitory mechanism. In further contrast to c-Src, additional inhibitory constraints are imposed onto c-AbI by the myristoylated cap binding directly to the C-terminal lobe of the kinase domain thus further locking an SH3-SH2 "clamp" onto the catalytic domain. This "molecular lock", however, does not exist in the nonmyristoylated form of c-AbI—1a, which contains only a partial cap region. A more comprehensive role of the cap region could not be discerned from the crystal structure of c-AbI, but the cap region is believed to play a role in regulating accessibility and binding of phosphotyrosine-containing peptides (Hantschel et al., 2003).

Various proteins that bind to c-AbI kinase have been proposed to be c-AbI co-inhibitors. The proteins F-actin, Pag and Rb have been hypothesized to act as passive co-inhibitors by stabilizing the auto-inhibited conformation of c-AbI (Wang, 2004). Another set of candidate c-AbI inhibitors, Abi1 and Abi2, were isolated in the search to identify c-AbI-binding partners (Dai and Pendergast, 1995; Shi et al., 1995) as well as in efforts to identify binding partners of the SH3 domain from other proteins, hence their names E3b1 (eps8 SH3 binding protein 1—Biesova et al., 1997) and Hssh3bp1 (human spectrin Src homology 3 domain binding protein 1—Ziemnicka-Kotula et al., 1998). The inhibitory role of Abi proteins in c-AbI kinase signaling has been proposed primarily based on the Abi1 and Abi2 inhibitory role in regulation of cell growth (Dai and Pendergast, 1995; Macoska et al., 2001; Shi et al., 1995), but the molecular mechanism of their action is not clear. Abi1 and Abi2 interact with c-AbI kinase C-terminal PXXP sequences in the proline rich linker, PRL (Dai and Pendergast, 1995; Shi et al., 1995) and with c-AbI SH3 domain (Ziemnicka-Kotula et al., 1998). Thus, one such mechanism might involve reinforcement of the c-AbI kinase autoinhibited conformation through cooperative binding of the Abi's PXXP sequences and SH3 domain to the c-AbI SH3 domain and PRL region. However, no SH2-based mechanism of kinase regulation has been demonstrated for c-AbI kinase and Abi proteins.

Based on the above discussion, characterization of the role of Abi proteins in c-AbI inhibition is needed. The present invention addresses this need.

SUMMARY OF THE INVENTION

Accordingly, the inventors have identified peptides derived from Abi proteins that inhibit AbI kinases. See Example.

Thus, the present invention is directed to purified compounds comprising SEQ ID NO:1, where the tyrosine at residue 10 is phosphorylated.

The present invention is also directed to purified compounds comprising SEQ ID NO:1, where the amino acid sequence of the compound is less than 400 amino acids.

The invention is additionally directed to methods of determining whether an agent is a candidate inhibitor of an AbI kinase. The methods comprise contacting one of the above-described compounds with the agent in the presence of the AbI kinase, and evaluating whether the compound is bound to the AbI kinase. In these methods, if the compound is not bound to the AbI kinase, then the agent is a candidate inhibitor of the AbI kinase, and if the compound is bound to the AbI kinase, then the agent is not a candidate inhibitor of the AbI kinase. The agents identified by these methods as inhibitors of an AbI kinase, and methods of inhibiting an AbI kinase by contacting the AbI kinase with those agents are also aspects of the present invention.

The invention is further directed to methods of inhibiting an AbI kinase. The methods comprise contacting the AbI kinase with one of the above-described compounds.

Additionally, the invention is directed to methods of treating a patient having a condition characterized by a mutant AbI kinase. The methods comprise administering any of the above compounds that inhibit the mutant AbI kinase to the patient.

The invention is also directed to methods of treating a patient at risk for a condition characterized by a mutant AbI kinase. The methods comprise administering any of the above compounds that inhibit the mutant AbI kinase to the patient.

The present invention is additionally directed to methods of labeling an AbI kinase. The methods comprise combining the AbI kinase with one of the above-described compounds, under conditions where the compound interacts with the AbI kinase. The compound used in these methods also has a detectable moiety.

The invention is also directed to methods of isolating an AbI kinase from a tissue. The methods comprise homogenizing the tissue, combining the homogenized tissue with one of the above described compounds that also has a binding moiety, and isolating the compound bound to the AbI kinase.

BRIEF DESCRIPTION OF THE DRAWINGS

FIG. 2 is graphs and photographs of western blots showing the identification of the minimal binding region of c-AbI SH3 and SH2 domains in the N-terminus of Abi1. Panel A shows binding to the c-AbI SH3 domain. Recombinant GST fusion polypeptides containing the N-terminal terminal region of Abi1/Hsshb3p1 were separated on SDS polyacrylamide gels and transferred onto a nitrocellulose membrane. The following Abi1 polypeptides were analyzed: N1-187, encoding residues 1-187; N1-172, encoding residues 1-172; N1-253, encoding residues 253; N1-253ΔEx6, encoding residues 1-253 but lacking exon 6 sequences of Abi1 (Macoska et al, 2001); GST, glutathione S-transferase. The bottom photograph of a western blot on the left shows results when probed with the anti-GST monoclonal antibody (Anti-GST) to indicate level of protein expression. The top photograph was incubated with a biotinylated GST-AbI-SH3 domain (GST-AbI-SH3-B). No binding to biotinylated GST (GST-B) was observed (middle panel). The graph shows relative binding of polypeptides, as percent of N1-253, quantified from three independent experiments (n=3, ±s.d.). Panels B-D show binding to the c-AbI SH2 domain. A surface plasmon resonance analysis was used to determine the interaction between biotinylated 14-residue peptides containing either phosphorylated tyrosine 213 (pY213) or nonphosphorylated tyrosine 213 (Y213) to GST-tagged AbI SH2 domain. Panel B shows the results when biosensor chips coupled with pY213 or Y213 peptides were injected with the AbI SH2 domain (1 μM); Panel C results when a pY213-coupled biosensor chip was injected with different concentrations of AbI SH2 domain, as indicated. Panel D shows the results when a pY213-coupled biosensor chip was injected with 0.5 μM of either the AbI SH2 domain or the AbI SH2 domain R171K mutant. No binding to the GST protein alone was observed (not shown). RU, response unit.

FIG. 4 shows western blots demonstrating that Y213 is phosphorylated by c-AbI kinase. Panel A shows that Y213 phosphorylation of recombinant Abi1 is dependent on expression of c-AbI kinase. Double AbI(−/−)Arg(−/−) knockout cells were either transfected with the wild type or mutant Abi1 plasmids alone, or co-transfected with Abi1 and c-AbI as indicated: wild type Abi1 (Abi1-Wt); Abi1 with the Y213F mutation (Abi1-F213); Abi1 mutant lacking exon 6 containing Y213 (Abi1-Δex6); Abi1 mutant containing the PXXP[181]AESEA[185] mutation (Abi1-Pro). Portions of cell lysates were immunoprecipitated with monoclonal anti-HA antibody, or K12 polyclonal antibody to c-AbI. Immunoprecipitated samples were separated on 4-12% Bis-Tris polyacrylamide gel and transferred onto a nitrocellulose membrane. The membrane was blotted first with the phosphospecific antibody to pY213 (pY213) (see also Panel B) followed by stripping and blotting with the polyclonal antibody to HA (Abi1-HA) followed by stripping and blotting with phosphospecific antibodies to pY213 (A) or PY99 (B). "c-AbI" shows levels of c-AbI expression (isoform 1b) obtained by blotting with 8E9. Panel B shows that the polyclonal antibody raised to the phosphotyrosine containing peptide pY213 is highly specific to Abi1 phosphorylated by c-AbI. Increasing amounts of the full-length GST-Abi1 were incubated with the baculovirus-purified c-AbI (+c-AbI) or without (−c-AbI) as described in the *Experimental Proce-* dures section of the Example, under *Kinase Assay*. Identical amounts of reaction mixtures (of increasing relative amounts 1.0×, 1.5×, 2.0×) were separated on SDS PAGE followed by blotting with the affinity purified antibody to phosphopeptide pY213 (pY213) or with the generic antibody to phosphotyrosine pY350 (pY350); "Abi1" indicates levels of GST fusion protein using polyclonal antibody to GST.

Figure 5:
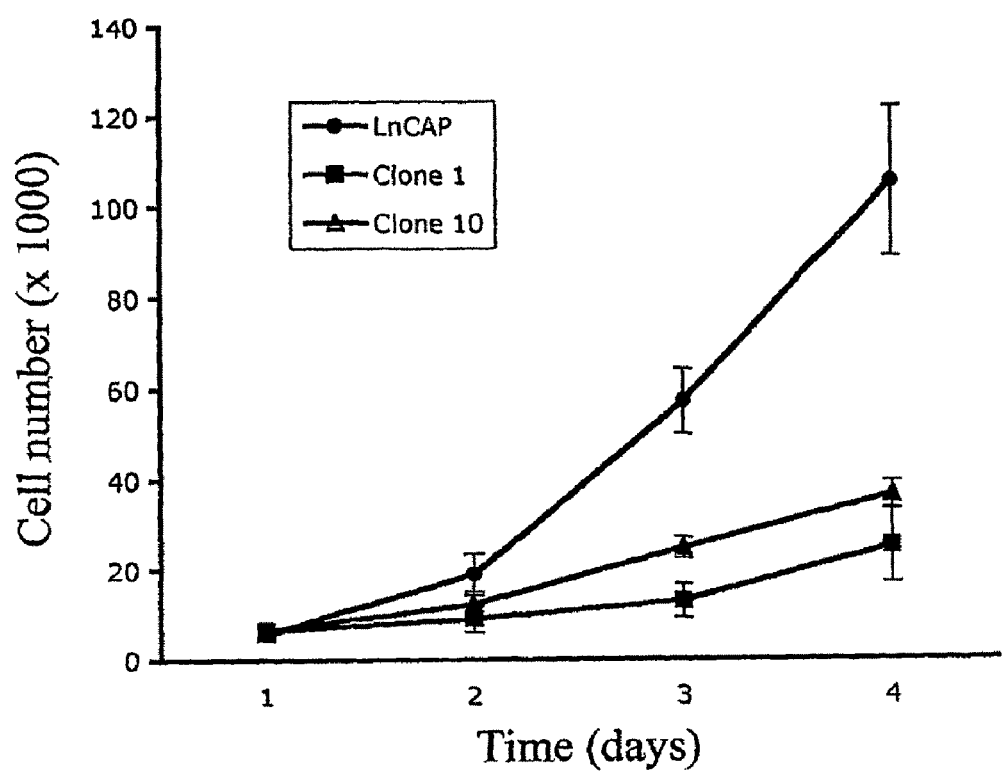

FIG. 5 is graphs and micrographs of cells showing the growth inhibition and inhibition of cell spreading activity of LnCAP cells supplemented with Abi1. Panel A is a graph showing the growth inhibition by Abi1. Growth rate was evaluated by counting number of cells at indicated time points following initial plating. LnCAP clones stably expressing recombinant Abi1: Abi (+) clone 1, Clone 1; Abi1(+) clone 10, Clone 10; LnCAP, wild type LnCAP cells. Vertical error bars represent ±s.d. (n=4). Panels B and C show the spreading activity of LnCAP cells. Panel B is representative images from live cell observations. The numbers at the bottom of each image indicate time elapsed (in hours) since plating. Panel C shows the percent of cells with spreading activity in the Abi1 transfected cell line and LnCAP cells, or LnCAP cells treated with STI-571. Cells with spreading activity in each group were evaluated at indicated time points; for LnCAP vs. Abi1(+) cell lines: 2 h, p=0.46; at 4 h -16 h p<0.001 ($\chi^2$); for untreated LnCAP vs. STI-571-treated LnCAP cells 2 h, p=0.40; at 4 h -10 h p<0.001 ($\chi^2$); at 12 -16 h p>0.05; number of cells at each time point n>100. LnCAP, wild type LnCAP cells; Abi1(+), clone 10; STI-571, LnCAP cell treated with STI-571. LnCAP cells were treated with STI-571 (3 µM) for 24 hrs prior to replating without the drug. Please note that with the increasing amount of time the inhibitory effect of the drug on cell spreading activity is decreasing.

FIG. 6 is graphs and photographs of western blots and stained gels showing the expression of Abi1 inhibits c-AbI kinase activity in LnCAP cells. c-AbI kinase activity was evaluated in wild-type (LnCAP) and an Abi (Abi1+) stably transfected cell line (clone 10). Panel A shows the expression levels of c-AbI kinase and Abi1. The left side shows a western blot where c-AbI (8E9) and Abi1 (Ab-2) were immunoprecipitated with K12 and 7B6, respectively, and blotted with the indicated antibodies. The graph on the right indicates expression levels of Abi1 in the cell lines (n=3; ±s.d.; p=0.2861). Panel B shows activities of c-AbI kinase immunoprecipitated from LnCAP cell lines. The left side shows a western blot where c-AbI kinase assays were carried out with GST-Crk as a substrate; reaction mixtures were separated on SDS-PAGE gels and blotted with an anti-phosphotyrosine antibody (PY99) or with anti-GST antibody (Anti-GST). "Anti-GST" indicates the GST substrate input in each reaction. "LnCAP" shows Crk phosphorylation in LnCAP. "Control" is the reaction mixture that was added to the control IgG immunoprecipitation from the LnCAP cell line. The graph shows Crk phosphorylation levels in the cell lines (±s.d.; n=3; p=0.0124). Panel C shows tyrosine phosphorylation in the LnCAP cell line supplemented with Abi1. The left side shows a western blot where c-AbI kinase was immunoprecipitated (K12 antibody) from cell lines and blotted with 8E9 (indicating the c-AbI protein level) or PY99 (indicating tyrosine phosphorylation on c-AbI) antibodies. "GAPDH" indicates lysate input levels used for immunoprecipitation. The right side shows the total cell lysates from the indicated cell lines separated on SDS-PAGE, then Coomassie stained ("Coomassie") or blotted and stained with the anti-phosphotyrosine antibody PY99. The graph shows the total phosphorylation levels in the cell lines (+s.d; n=3; p=0.0101). Panel D shows that Abi1 interacts with c-AbI kinase. Abi1 was immunoprecipitated from indicated cell lines and the immunoprecipitated proteins were analyzed by Western blotting using specific antibodies: Ab-2 (Abi1); K-12 (c-AbI-coIP). "c-AbI-IP" represents levels of c-AbI kinase in the cell lines following immunoprecipitation with K-12 antibody followed by blotting with 8E9. "pY213" represents immunoreactivity of phosphorylated Abi1 at Y213. Immunoprecipitated Abi1 was loaded at equal levels for the comparison. All cell lines were treated with prevanadate before lysis and immunoprecipitation as described in the *Experimental Procedures* section of the Example.

FIG. 7 is graphs and photographs of western blots showing that Abi1 regulates cell growth and cell spreading by regulation of c-AbI kinase activity. Panel A shows that expression of the wild type but not Y213F or the $^{181}$AESEA$^{185}$ mutant of Abi1 inhibits c-AbI tyrosine kinase activity in LnCAP cells. Cell lines stably expressing wild type or mutants of Abi1 were examined for c-AbI kinase activity. The kinase activity was evaluated by examination of phosphorylation levels of the endogenous AbI substrate Crk (pY-Crk); levels of the c-AbI activation loop phosphotyrosine pY412 (pY412). Total tyrosine phosphorylation of c-AbI (PY99) was also examined as indicated. Proteins were immunopreciptated from indicated stable cell lines: c-AbI with antibody K-12, Crk with anti-Crk, Abi1 with antibody 7B6. Expression of the recombinant Abi1 in cell lysates was evaluated with an anti-HA antibody (Abi1-HA Lys); expression of total Abi1 in Abi1(+) and LnCAP cell lines was evaluated by blotting of the immunoprecipitated Abi1 with the polyclonal antibody Ab-2 (Abi1-IP). The graph on the right indicates quantitation of c-AbI kinase activity in the cell lines (n=3; ±s.d.). Crk phosphorylation is lower in Abi1(+) than in the LnCAP cell line (p<0.001). It is also lower in Wt.Ha than in F213.Ha or Pro.Ha (p<0.001). Differences of pY412 or PY99 phosphorylation among the groups are also significant (p<0.01). Panel B shows that the Y213 and $^{181}$PPSPP$^{185}$ sequences of Abi1 regulate growth rates of stably transfected LnCAP cell lines. Growth rates of LnCAP clones were evaluated by counting cell number at indicated time points following initial plating (n=3; bars indicate s.e.m.). Two Way ANOVA analysis taking into consideration all 4 days of observation indicated that Abi1-Pro cell lines proliferated with faster rate than Abi1-wt, Abi1(+), or Abi1-F213 cell lines (p<0.05); Abi1-wt, Abi1(+), and Abi1-F213 were not different from each other (p>0.05); LnCAP and Mock were not different from Abi1-Pro (p>0.05). Panel C shows the regulation of cell spreading by Abi1. LnCAP cells were plated on collagen. Observations were carried at 6 hrs following the plating. Mean area was evaluated in each clone (n=20; bars indicate s.e.m.); duplicate clones for the HA-tagged Abi1 expressing cell lines were evaluated. Clones expressing wild type Abi1 showed significant decreases in the mean cell area vs. LnCAP cells alone: Abi1(+), p<0.0001; Wt.Ha-1, p=0.0002; Wt.Ha-2, p=0.007. Other Abi1 clones did not exhibit significant differences in cell spreading in comparison to LnCAP. The following LnCAP cell lines were analyzed: cell lines stably expressing wild type untagged Abi1, Abi1(+), or Ha-tagged Abi1 (Wt.Ha-1 and Wt.Ha-2); Ha-tagged Abi1 mutants Abi1 Y213F (F213.Ha-1 and F213.Ha-2) and Abi1-$^{181}$AESEA$^{185}$ (Pro.Ha-1 and Pro.Ha-2); wild type LnCAP cell line (LnCAP); and LnCAP cell line transfected with unmodified plasmid (Mock). For cell growth and cell spreading assays duplicate clones expressing HA-tagged Abi1 were evaluated; for AbI kinase activity (FIGS. 7A and B) Wt.Ha-1 (Wt.Ha), F213.Ha-1 (F213.Ha), and Pro.Ha-1 (Pro.Ha) were evaluated. "GAPDH" indicates level of proteins in cell lysates.

FIG. 8 shows models of c-AbI regulation by Abi1 phosphopeptides. Panel A shows the modeled phosphorylated peptide binding to the SH2 domain of c-AbI kinase. The phosphotyrosine residue 213 (pY213) of the modeled peptide is shown in the binding pocket of the SH2 domain. Three arginines, R153, R171 and R194 (green) of the SH2 domain of c-AbI kinase are in the close proximity to the pY213 residue of the phosphor peptide for possible interactions. All helices are shown in cylindrical faun (turquoise). The αI' helix of inactive c-AbI kinase is labeled. The dotted cylinder indicates the position of the same helix in the active form (aI helix) (Nagar et al., 2003), which shows possible clashes with the SH2 domain. The loop in the c-AbI kinase structure representing residues S173-Q179 has been deleted for clarity. The figure was created using PyMOL software (DeLano Scientific LLC, South San Francisco, Calif.). Panel B is a schematic model illustrating the regulation of c-AbI kinase by pY213 and Pro-pY213. The upper drawings show the regulated structure of c-AbI with major elements of autoinhibition as determined by crystal structure (Hantschel et al., 2003; Nagar et al., 2003): SH3 domain interacts with SH2-CD linker and CD; SH2 domain interacts with CD. In the myristoylated form of the kinase the C-terminal helix of CD, αI', forms a binding pocket for myristate. Activation of c-AbI by several mechanisms, which include disassociation of myristate (Hantschel et al., 2003; Nagar et al., 2003), lead to phosphorylation of SH2-CD linker and the activation loop. These events result in uncoupling of SH2 and SH3 domains from the CD, the C-terminal helix is now αI and partially occludes the SH2 phosphotyrosine-binding site. Binding of pY213 to AbI SH2 domain inhibits the kinase probably by stabilizing the C-terminal helix in the new αI'-like conformation (this is supported by the molecular modeling data, Panel A). The lower drawings show binding of Pro-pY213 leading to initial transient activation of the kinase due to displacement of SH3 and SH2 domains from the CD domain. This leads to formation of Pro-pY213-AbI complexes containing an elongated activated AbI with SH2 domain docked onto N lobe of the CD domain as suggested by Nagar et al. (2006). This is followed by the formation of less active and inactive Pro-pY213-AbI complexes. Positioning of αI'-like helix is postulated based on pY213 modeling. The small compound, GNF-2, reinforces the similar conformation of αI'-like helix by binding to the myristoyl binding pocket (Adrian et al., 2006), thus acting like myristoyl group. SH3, Src homology 3 domain; SH2, Src homology 2 domain; CD, catalytic domain. The N-terminal cap region and the C-terminal half of the c-AbI molecule were omitted for clarity.

Figure 9:
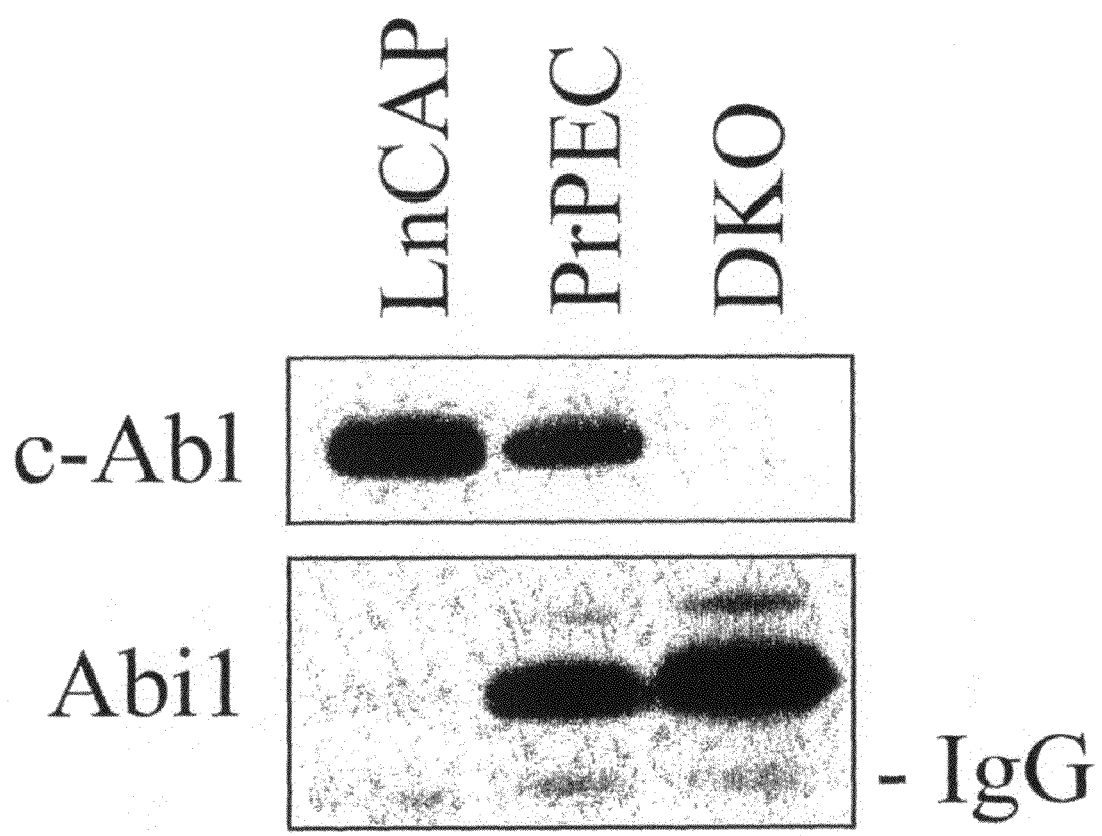

FIG. 9 is photographs of western blots showing that the expression level of Abi1 is reduced in LnCAP cells in comparison to primary prostate cells and a AbI(−/−) Arg(−/−) double knockout cell line. Abi1 was immunoprecipitated from lysates of indicated cell lines with monoclonal antibody 7B6 and blotted with polyclonal antibody Ab-2 to Abi1; c-AbI kinase was immunoprecipitated with K12 and blotted with monoclonal antibody 8E9. LnCAP, indicates the LnCAP cell line; PrPEC, indicates the a prostate cell line; DKO, indicates the AbI(−/−) Arg(−/−) double knockout cell line. IgG indicates a cross-reactive IgG band.

Figure 10:
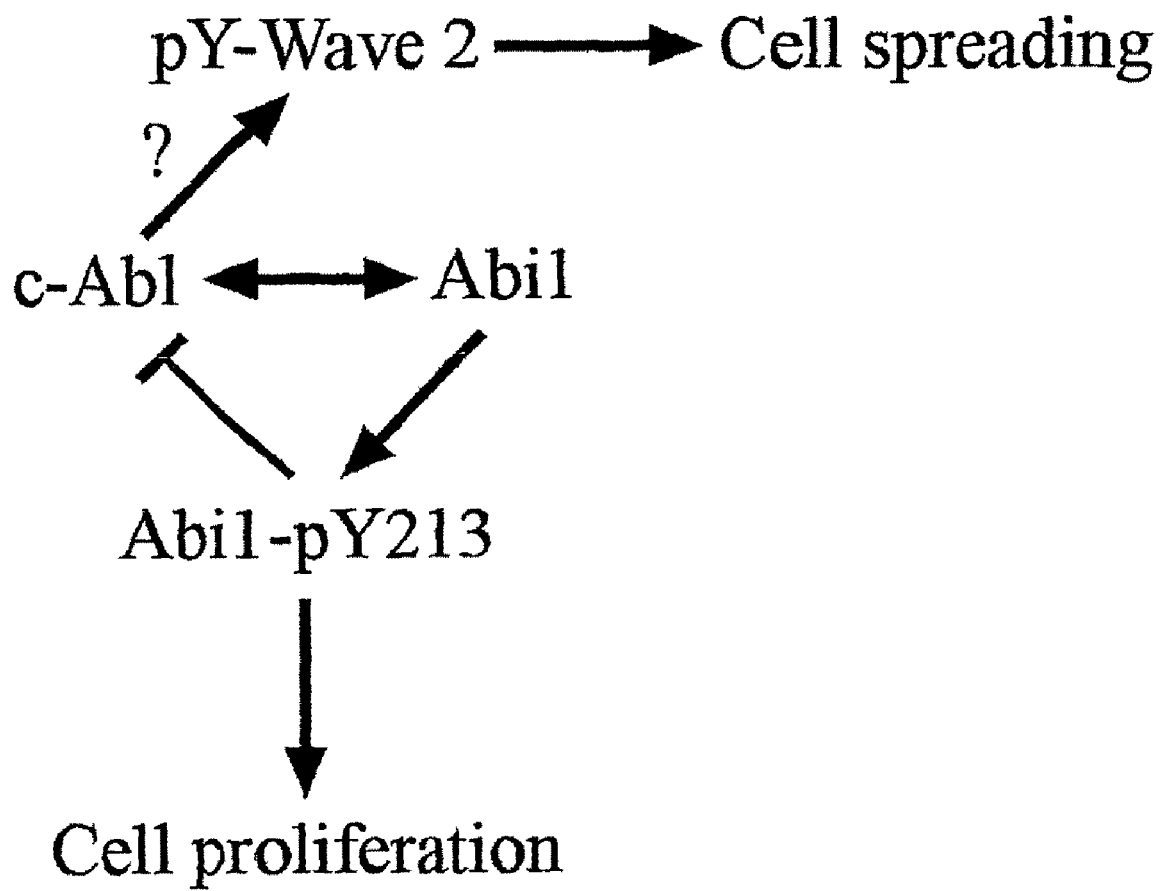

FIG. 10 is a diagram illustrating growth and cell-spreading regulation by cAbI and Abi1.

DETAILED DESCRIPTION OF THE INVENTION

Accordingly, the inventors have identified peptides that inhibit AbI kinases. The peptides are from proline-rich regions of Abi proteins. See Example.

Thus, the present invention is directed to purified compounds comprising SEQ ID NO:1, where the tyrosine at residue 10 is phosphorylated. SEQ ID NO:1 is a consensus sequence of an AbI kinase-interacting region of Abi1, Abi2 and Abi3. The Appendix of this application provides amino acid sequences of Abi1, Abi2 and Abi3 as SEQ ID NO:2, SEQ ID NO:3, and SEQ ID NO:4, respectively. The interacting regions of those proteins that are part of SEQ ID NO:1 are underlined in the Appendix and are also provided herein as SEQ ID NO:5 (Abi1) and SEQ ID NO:6 (Abi2 and Abi3). Thus, the compounds of the present invention can also comprise the amino acid sequence of SEQ ID NO:5 or SEQ ID NO:6. Longer versions of the AbI kinase interacting compounds of the invention are provided as SEQ ID NO:7 (a consensus sequence [FIG. 10]) and SEQ ID NO:8. Compounds comprising SEQ ID NO:7 or SEQ ID NO:8 are preferred because the PXXP AbI kinase binding motif is present therein, allowing for a more effective inhibition of AN kinases. Preferably, the compound comprises SEQ ID NO:8, which was utilized as described in the Example as an effective AbI kinase inhibitor.

The various 14-mer peptides represented by SEQ ID NO:1 are inhibitors of AbI kinases either as the small peptides themselves or as a large Abi protein (human sequences represented by SEQ ID NO:2, SEQ ID NO:3 and SEQ ID NO:4). Additionally, any chemical or macromolecule comprising any of the 14-mer peptides of SEQ ID NO:1 would be expected to inhibit an AbI kinase. Non-limiting examples of such chemicals or macromolecules include any protein (e.g., enzymes or cytokines), protein-nucleic acid hybrids, glycoproteins, proteoglycans, lipoproteins, and functional moieties such as a fluorescent molecule or antigen. The AbI kinase-inhibitory properties of any particular macromolecule comprising the 14-mer can be tested by any known method, including the methods described in the Example below.

Preferably, the compound comprises an amino acid sequence that is at least 85% homologous to at least a portion of SEQ ID NO:2, SEQ ID NO:3 or SEQ ID NO:4. The compound also preferably comprises an amino acid sequence that is completely homologous to at least a portion of a naturally occurring Abi1, Abi2, or Abi3. Such naturally occurring Abi1, Abi2 or Abi3 would be expected to be at least 85% homologous to SEQ ID NO:2, SEQ ID NO:3 or SEQ ID NO:4. More preferably, the compound comprises an amino acid sequence that is completely homologous to at least a portion of SEQ ID NO:2, SEQ ID NO:3 or SEQ ID NO:4, most preferably SEQ ID NO:2.

The compound can comprise an amino acid sequence of any length 14 amino acids or longer, including less than 400 amino acid residues, less than 100 amino acid residues, and less than 20 amino acid residues. The amino acid sequence is preferably 14 amino acid residues. Particular amino acid sequences envisioned for the compound are SEQ ID NO:1, SEQ ID NO:5, SEQ ID NO:6, SEQ ID NO:7, and SEQ ID NO:8. It is also preferred that the compound comprise a PXXP binding motif of a wild-type Abi1, Abi2 or Abi3 that is not within SEQ ID NO:1.

Some compounds envisioned as part of the invention have at least one amino acid represented by a peptidomimetic. Such compounds are known to often be more resistant to degradation in vivo than the corresponding compounds having all naturally occurring amino acids.

Preferably, the compound can inhibit activity of an AbI kinase. Most preferably, such compounds inhibit AbI kinases when administered to mammals, particularly when the inhibited AbI kinase causes disease, such as BCR-AbI.

The compounds can also comprise a detectable moiety or a binding moiety. While the invention is not narrowly limited to the compounds with any particular detectable moiety or binding moiety, the detectable moiety or binding moiety is preferably a radioactive moiety, an antigen, a fluorescent moiety, or a His6 moiety. For many applications, the detectable moiety or binding moiety is most preferably a fluorescent moiety. In some of these applications, the detectable fluorescence of the fluorescent moiety changes intensity when the compound is combined with an AbI kinase.

For therapeutic applications, the compounds of the present invention should be in a pharmaceutically acceptable composition.

The invention is also directed to purified compounds comprising SEQ ID NO:1, where the amino acid sequence of the compound is less than 400 amino acids. Preferred compounds include those that comprise SEQ ID NO:5, SEQ ID NO:6, SEQ ID NO:7, or SEQ ID NO:8. Preferably, the compounds comprise an amino acid sequence that is at least 85% homologous to at least a portion of SEQ ID NO:2, SEQ ID NO:3 or SEQ ID NO:4. More preferably, the compounds comprise an amino acid sequence that is completely homologous to at least a portion of a naturally occurring Abi1, Abi2 or Abi3. Also preferred are compounds that comprise an amino acid sequence that is completely homologous to at least a portion of SEQ ID NO:2, SEQ ID NO:3 or SEQ ID NO:4, most preferably SEQ ID NO:2.

The amino acid sequence of the compound can be any length less than about 400 amino acids, such as less than 100 amino acid residues, or less than 20 amino acid residues. A preferred length is 14 amino acid residues. In particular, the compound can consist of SEQ ID NO:1, SEQ ID NO:5, SEQ ID NO:6, SEQ ID NO:7 or SEQ ID NO:8. As in the previously described compounds, these compounds can comprise a peptidomimetic as at least one amino acid of the amino acid sequence. Preferably, the compound comprises a PXXP binding motif of a wild-type Abi1, Abi2 or Abi3, generally PPSPP (SEQ ID NO: 17), that is not within SEQ ID NO: 1. The compound can also be phosphorylated at the tyrosine at residue 10 of SEQ ID NO: 1. It is also preferred that the compound can inhibit activity of an AbI kinase.

These compounds can also comprise a detectable moiety or a binding moiety. For therapeutic applications, these compounds should be in a pharmaceutically acceptable composition.

Because the above-described compounds inhibit AbI kinases by their interaction with those enzymes, an agent that prevents that interaction would be a candidate inhibitor of the AbI kinase. The interaction of the compound with the AbI kinase is most usefully measured by evaluating binding of the compound to the AbI kinase. Thus, the invention is additionally directed to methods of determining whether an agent is a candidate inhibitor of an AbI kinase. The methods comprise contacting one of the above-described compounds with the agent in the presence of the AbI kinase, and evaluating whether the compound is bound to the AbI kinase. In these methods, if the compound is not bound to the AbI kinase, then the agent is a candidate inhibitor of the AbI kinase, and if the compound is bound to the AbI kinase, then the agent is not a candidate inhibitor of the AbI kinase.

Preferably, the compound used in these methods further comprises a detectable moiety, to more easily evaluate binding of the compound to the AbI kinase. The AbI kinase can alternatively comprise a detectable moiety for this purpose. Preferred detectable moieties are radioactive moieties, antigens, or fluorescent moieties. Most preferably, the detectable moiety is a fluorescent moiety.

In some forms of these methods, the detectable fluorescence of the fluorescent moiety changes intensity when the compound is combined with an AbI kinase. The skilled artisan could select a fluorescent compound and its binding position on the compound and/or the AbI kinase to effect these methods without undue experimentation. In these methods, evaluation of compound binding to the AbI kinase is by measuring fluorescence intensity, where an increase in fluorescence intensity with the compound over fluorescence intensity without the compound indicates the compound is not bound to the AbI kinase.

Binding of the compound to the AbI kinase can also be evaluated by measuring the apparent size of the peptide or AbI kinase under non-denaturing conditions, by, e.g., gel electrophoresis or column chromatography.

Upon identification of a candidate inhibitor, that inhibitor is preferably further tested by assessing kinase activity of the AbI kinase in the presence of a candidate inhibitor, where an AbI kinase inhibitor would reduce the activity of the AbI kinase.

The present invention also encompasses agents identified by the above methods. Additionally, the invention encompasses methods of inhibiting an AbI kinase comprising contacting the AbI kinase with the inhibitory agent identified by the above methods.

The invention is further directed to additional methods of inhibiting an AbI kinase. The methods comprise contacting the AbI kinase with one of the above-described compounds. Preferably, the compound consists of SEQ ID NO:1, SEQ ID NO:5, SEQ ID NO:6, SEQ ID NO:7 or SEQ ID NO:8. It is also preferred that the AbI kinase is in a mammalian cell. Preferably, the mammalian cell is part of a living mammal. More preferably, the mammal has, or is at risk for, a condition characterized by a mutant AbI kinase. An example of such a condition is cancer. Preferably, the cancer is chronic myelogenous leukemia (CML) or prostate cancer.

Additionally, the invention is directed to methods of treating a patient having a condition characterized by a mutant AbI kinase. The methods comprise administering any of the above compounds that inhibit the mutant AbI kinase to the patient. Preferably, the compound is administered parenterally to the patient. For these methods, the condition is preferably chronic myelogenous leukemia or prostate cancer.

The invention is also directed to methods of treating a patient at risk for a condition characterized by a mutant AbI kinase. The methods comprise administering any of the above compounds that inhibit the mutant AbI kinase to the patient.

The present invention is additionally directed to methods of labeling an AbI kinase. The methods comprise combining the AbI kinase with one of the above-described compounds, under conditions where the compound interacts with the AbI kinase. The compound used in these methods also has a detectable moiety as described above. The AbI kinase labeled in these methods can be part of a mammalian tissue, for example a biopsy. The biopsy tissue can be homogenized either before or after labeling, allowing the AbI kinase to be quantified by quantifying the amount of detectable label present in protein from the homogenized tissue that is the size of the AbI kinase/compound combination. The labeled tissue can also be subjected to histological analysis, for example when it is desired to localize or quantify the AbI kinase in a cell and/or in the biopsy.

The invention is also directed to methods of isolating an AbI kinase from a tissue. The methods comprise homogenizing the tissue, combining the homogenized tissue with one of the above described compounds that also has a binding moiety, and isolating the compound bound to the AbI kinase. The skilled artisan could perform these methods without undue experimentation using known procedures. If the AbI kinase need be further characterized, the compound can be separated from the AbI kinase by, e.g., salt treatment. The isolated AbI kinase can also be quantified by any method known in the art.

The above peptides that inhibit AbI kinase can be used for that purpose, either in vitro or in vivo, e.g., in a patient with chronic myelogenous leukemia.

Preferred embodiments of the invention are described in the following Example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE

Inhibition of c-AbI Kinase by Peptides Derived from Abi1/Hssh3bp1

Example Summary

Unlike c-Src, the autoinhibitory mechanism of c-AbI tyrosine kinase regulation does not include an inhibitory phosphotyrosine located in cis. Here we report identification of an allosteric non-ATP-competitive mechanism of c-AbI kinase inhibition by a phosphotyrosine located in trans in Abi1/Hssh3bp1. The mechanism involves high affinity binding of the phosphotyrosine to the AbI SH2 domain and PXXP motif to the AbI SH3 domain, thus implying negative feedback inhibition by phospho-Abi1. The critical role of Abi1 in regulation of c-AbI kinase activity in vivo is supported by inhibition of the kinase activity in cells upon expression of the wild type but not the Y to F mutant of Abi1. Furthermore, the data suggest that cell proliferation is controlled by the presence of Abi1 regulatory tyrosine. However, cell spreading is regulated by Abi1-dependent c-AbI tyrosine kinase activity and not by the tyrosine per se. Molecular modeling suggests that binding of the phosphotyrosine to c-AbI stabilizes autoinhibited conformation of the kinase. These findings suggest a novel mechanism by which AbI kinases are regulated in cells and provide a novel strategy for anti-leukemic drug development.

Introduction

The ubiquitous nonreceptor tyrosine kinase, c-AbI kinase, functions downstream of platelet-derived growth-factor receptor, integrin, or cytokine signaling, balancing events leading to apoptosis or to increased cell proliferation (Koleske et al., 1998; Woodring et al., 2003). The critical role of c-AbI kinase in cell proliferation is illustrated by the dramatic manifestation of chronic myelogenous leukemia (CML) due to expression of BCR-AbI, a kinase-activated mutant form of c-AbI tyrosine kinase (Druker et al., 2001a; Goldman and Melo, 2003). BCR-AbI is a fusion protein resulting from the chromosomal translocation and fusion of BCR to c-AbI, which effectively leads to disregulation of the kinase activity. Rational approaches to curtail this activity led to the development of STI-571 (imanitib mesylate, or Gleevec) (Buchdunger et al., 1996) as the successful treatment of CML (Druker et al., 2001b; Druker et al., 1996) and some other types of cancer. STI-571, which inhibits kinase due to its competition with ATP and stabilization of the inactive kinase conformation (Schindler et al., 2000), has provided a template for the anti-kinase drug development for cancer therapies. A number of anti-kinase compounds are now in clinical trials (Garber, 2006) including second generation of anti-AbI drugs (Shah et al., 2004 ; Weisberg et al., 2005) leading to hopes of long-term remissions following treatment of CML (O'Hare et al., 2005). Success of anti-AbI inhibitors has been held back by appearance of drug-resistance mutations (Gone et al., 2001; von Bubnoff et al., 2002), leading to re-thinking of the mechanism of Bcr-AbI regulation (Al-Mi et al., 2004; Khorashad et al., 2006; Miething et al., 2006). This has brought the attention back to c-AbI, since Bcr-AbI and c-AbI share most regulatory domains (Hantschel and Superti-Furga, 2004; Woodring et al., 2003).

Auto-inhibition has emerged as the major mechanism of regulation of c-Src and c-AbI (Courtneidge, 2003; Hantschel et al., 2003; Nagar et al., 2003; Pluk et al., 2002; Thomas and Brugge, 1997; Wang, 2004). These kinases share high structural homology conferred by the presence of highly conserved structural domains: SH3, SH2, and the catalytic domain. Crystal structures of c-Src (Williams et al., 1997; Xu et al., 1999) and c-AbI (Hantschel et al., 2003; Nagar et al., 2003) reveal that SH3 and SH2 domains bind to the catalytic domain (CD), and induce the autoinhibitory conformation, thus providing the basic mechanism of regulation of these kinases. This basic regulation is preserved in BCR-AbI since it contains all of the c-AbI domains downstream from and including the SH3 domain.

c-Src and c-AbI differ from each other in two mechanisms that inhibit activities of these kinases. In c-Src, the inhibition is achieved by intramolecular interaction of the SH2 domain with the phosphorylated tyrosine 527 located in C-terminus on the same molecule (Thomas and Brugge, 1997). In c-AbI there is no internal phosphotyrosine-SH2 domain interaction, precluding this inhibitory mechanism. In further contrast to c-Src, additional inhibitory constraints are imposed onto c-AbI by the myristoylated cap binding directly to the C-terminal lobe of the kinase domain, and by the cap region phosphoserine 69 binding to the SH2 domain (Nagar et al., 2006). These interactions are further locking the SH3-SH2 "clamp" onto the catalytic domain. Myristoyl group (Hantschel et al., 2003; Nagar et al., 2003), or small compounds mimicking its action (Adrian et al., 2006), stabilize the position of the C-terminal helix of the catalytic domain, at resulting in the inhibitory conformation of the kinase. The "molecular lock" imposed by the myristoylated cap, however, does not exist in the nonmyristoylated form of c-AbI—isoform 1 a, which contains only a partial cap region, or in BCR-AbI, where it is replaced by BCR. Thus, the myristoylated cap does not regulate kinase activities of BCR-AbI, or the c-AbI-la, although the phosphoserine 69 is preserved in the latter, where it may contribute to the autoinhibitory mechanism (Nagar et al., 2006). Intramolecular interactions of the cap region are also likely to regulate accessibility, and thus binding of AbI SH3 or SH2 ligands including phosphotyrosine-containing peptides from growth factors, which may play a role in AbI activation (Hantschel et al., 2003). Considering the complexity of AbI regulation, activation of the kinase activity is likely to involve multiple steps leading to uncoupling of SH3 and SH2 domains from the catalytic domain and "freeing" the kinase from inhibition.

Various proteins that bind to c-AbI kinase have been proposed to be c-AbI co-inhibitors. The proteins F-actin, Pag and Rb have been hypothesized to act as passive co-inhibitors by stabilizing the auto-inhibited conformation of c-AbI (Wang, 2004). Another set of candidate c-AbI inhibitors, Abi1 and Abi2, were isolated in the search to identify c-AbI-binding partners (Dai and Pendergast, 1995; Shi et al., 1995) as well as in efforts to identify binding partners of SH3 domain from other proteins hence their names E3b1 (Biesova et al., 1997), or Hssh3bp1 (Ziemnicka-Kotula et al., 1998). The inhibitory role of Abi proteins in c-AbI kinase signaling has been proposed primarily based on the Abi1's and Abi2's inhibitory role in regulation of cell growth (Dai and Pendergast, 1995; Macoska et al., 2001; Shi et al., 1995) but the molecular mechanism of their action is not clear. The LnCAP prostate tumor cell line contains a heterozygous mutation in the Abi1 gene that results in deletion of exon 6, pointing to the possibility that this might be the critical growth-regulatory region of Abi1 (Macoska et al., 2001). Abi1 and Abi2 interacts with c-AbI kinase C-teminal PXXP sequences in the proline rich linker, PRL (Dai and Pendergast, 1995; Shi et al., 1995), and with c-AbI SH3 domain (Ziemnicka-Kotula et al., 1998). Thus, one mechanism of growth regulation might involve regulation of c-AbI kinase by the reinforcement of c-AbI kinase autoinhibited conformation through cooperative binding of Abi's PXXP sequences and SH3 domain, to the c-AbI SH3 domain and PRL region. No SH3- or SH2-based mechanism of kinase regulation, however, has been demonstrated for c-AbI kinase and Abi proteins. In addition, STI-571-resistant mutations have been found in AbI SH3 and SH2 domain (Azam et al., 2003), suggesting the possibility, that, if Abi proteins regulate AbI catalytic activity through binding to these domains, they may be important in regulating STI-571 resistance in vivo.

Reported here is the discovery of a new allosteric mechanism of c-AbI kinase inhibition by phosphopeptides derived from the AbI SH3 and SH2-binding region of Abi1. Molecular modeling suggests that phosphopeptides stabilize the autoinhibited conformation of the c-AbI kinase leading to a conformation similar to this observed with the myristoyl group and the SH2 domain bound to the C-lobe of AbI catalytic domain. It is proposed that the mechanism of kinase inhibition demonstrated here may be used as a novel method of development of allosteric inhibitors of AbI and Bcr-AbI kinases.

Figure 1:
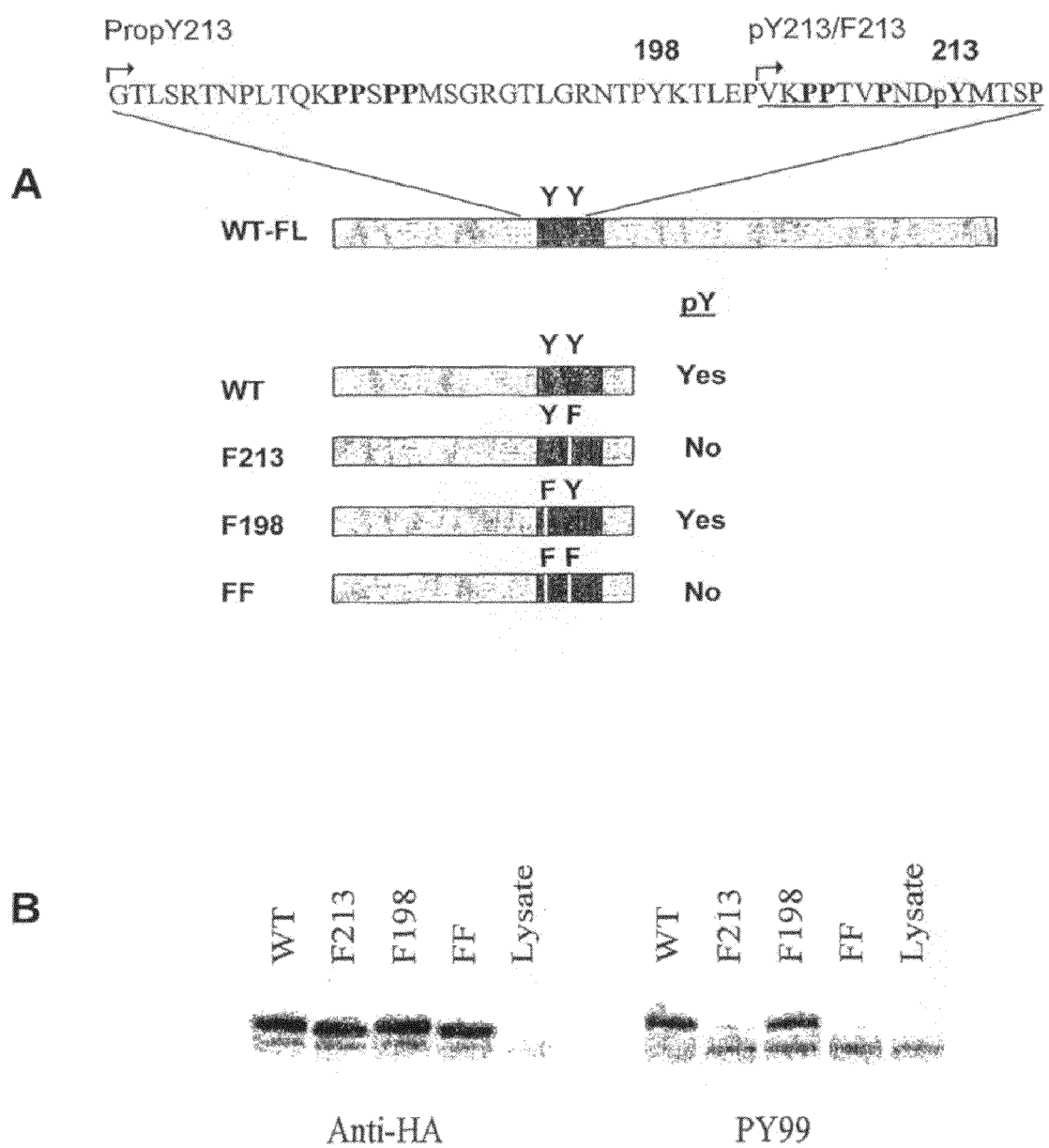
FIG. 1 is diagrams and photographs of western blots showing the identification of Abi1 Y213 as a c-AbI kinase phosphorylation site. Panel A shows the regulatory region of Abi1. At the top is a diagram of peptides used in the study. Below that diagram is the sequence of Abi1 containing the regulatory tyrosine 213 (residues 169 to 217, GenBank Accession No. U87166). The names of the peptides used in the experiments described in the Example are above the lines depicting the specific peptide. Pro stands for inclusion of the PXXP motif, PPSPP; Y, indicates tyrosine; pY, indicates phosphotyrosine, F, indicates a tyrosine to phenylalanine replacement. The N-terminus of peptides Pro-pY213, pY213, and F213 peptides used in kinase assays is marked above the sequence with a hooked arrow. Peptides Pro-Y198 and Pro-F198 span residues 169-203; these peptides exclude pY213 sequence. Peptide EE-Y198 contains the sequence PESEP instead of PPSPP that results in the loss of PXXP SH3-binding motif At the bottom of Panel A is a diagram depicting in vitro translated polypeptides used initially to characterize tyrosine phosphorylation of the N-terminus of Abi1. Polypeptides (rectangles) containing specific tyrosine (Y) to phenylalanine (F) replacements are schematically represented below the wild type full-length protein. The mutations replace either or both tyrosine residues, Y198, and Y213, in the region of interest. Kinase assay results for each polypeptide are given on the right. The dark-shaded area represents exon 6 of Abi1 lacking in LnCAP cells. Panel B shows western blots demonstrating tyrosine phosphorylation of the in vitro translated N-terminus of Abi1. Abi1 polypeptides containing the N-terminal half of the protein and indicated mutations of tyrosine residues were subjected to in vitro kinase reactions with c-AbI tyrosine kinase. Polypeptides were separated on SDS-Tricine polyacrylamide gels (7%) followed by blotting onto a PVDF membrane. The left blot shows the membrane blotted with anti-HA antibody. The HA epitope was introduced at the C-terminus of each polypeptide. The right blot shows the same polypeptides blotted with the anti-phosphotyrosine antibody PY-99. WT, wild type polypeptide; F213, polypeptide containing a phenylalanine replacement of tyrosine 213 (Y213F); F198, the polypeptide containing phenylalanine replacement of tyrosine 198 (Y198F); FF, the polypeptide containing Y213F and Y198F; Lysate, lysate with no Abi1 cDNA.

Results c-AbI phosphorylates Y213 of Abi1 in vitro. In the search for tyrosine phosphorylation sites of Abi1 we determined that candidate tyrosine residues, Y198 and Y213, are located within the proline-rich region of Abi1 previously demonstrated to bind AbI SH3 domain (Ziemnicka-Kotula et al., 1998). Using in vitro translated polypeptides encoding the N-terminal half of the protein it was determined that Y213 is the preferred site of phosphorylation by AbI kinase in vitro (FIG. 1). The phosphorylation site at Y213 was confirmed by mass spectroscopy of tryptic peptides following kinase reactions containing the recombinant Abi1 and active c-AbI (Table 1).

TABLE 1

Y213 phosphorylation by mass spectroscopy.

| Sample | [M + H]⁺ Nonphospho | [M + H]⁺ Nonphospho/ Met-O‡ | [M + H]⁺ Phospho | [M + H]⁺ Phospho/ Met-O |
|---|---|---|---|---|
| WT Predicted | 2213.1270 | 2229.1270 | 2293.1270 | 2309.1270 |
| WT no c-AbI | 2214.76 | 2229.62 | ND | ND |
| WT with c-AbI | 2213.27 | 2229.33 | 2294.08 | 2308.85 |
| T15WS no c-AbI | 2213.09 | 2229.13 | ND | ND |
| T15WS with c-AbI | 2213.69 | 2229.15 | 2293.39 | 2309.38 |
| F213* Predicted | 2197.1321 | 2213.1321 | Not Applicable | Not Applicable |
| F213 with c-AbI | 2197.27 | 2213.21 | ND | ND |

Samples were analyzed following trypsin digestion. Predicted and experimental masses for specific ions containing indicated tyrosine 213 or phenylalanine replacement are listed. The sequence for the wild type (WT) tryptic peptide is TLEPVKPPTVPNDpYMTSPAR (SEQ ID NO: 14); the phosphotyrosine 213 is in bold. *F213: same as WT but with Y213F replacement, in bold: TLEPVKPPTVPND-FMTSPAR (SEQ ID NO: 15). TI 5WS contains residues 144-303 of Abi1 isoform 4 (Ziemnicka-Kotula et al, 1998) and includes the same tryptic peptide as WT. ‡Met-O: depicts oxidized methionine (underlined in tryptic fragments above) that was present in all samples; therefore two (nonphospho-sample) or four (phospho-sample) species of molecules were observed. Method. Samples were phosphorylated by AbI kinase from New England Biolabs, TI 5WS, or by baculovirus-purified AbI, isoform 2. Proteins were separated on 4-12% Bis-Tris gel (Invitrogen, Carlsbad, CA) following 30 min of kinase reaction. Specific protein bands were isolated and subjected to trypsin degradation (Sigma-Aldrich Corp., St. Louis, MO), and following acidification of the samples with 0.5% TFA, ZIP TIP-18 (Millipore Corporation, Bedford, MA) was used to concentrate the samples and eluted with 0.1% TFA and 50% acetonitrile into tubes containing α-cyano-4-hydroxycinnamic acid matrix (Sigma-Aldrich Corp., St. Louis, MO) in 50% acetonitrile and 0.5% TFA. Mass spectrometric analyses were performed using an Applied Biosystems (Foster City, Calif.) Voyager DE MALDI mass spectrometer. Spectra were calibrated against an external or internal standard as needed. Identification of the minimal AbI SH3 and SH2 domain binding sites of Abi1. Initially, binding of the c-AbI SH3 domain was located to residues 144-260 of Abi1 (Ziemnicka-Kotula et al., 1998). The AbI SH3 binding was subsequently mapped to sequences of Abi1 containing PXXP SH3 binding motifs located upstream from tyrosine 213. Deletion of residues 173 through 187 of Abi1 containing the PXXP sequence, 18 IPPSPPI 85, completely abolished the binding to AbI SH3 domain (FIG. 2A).

Figure 3:
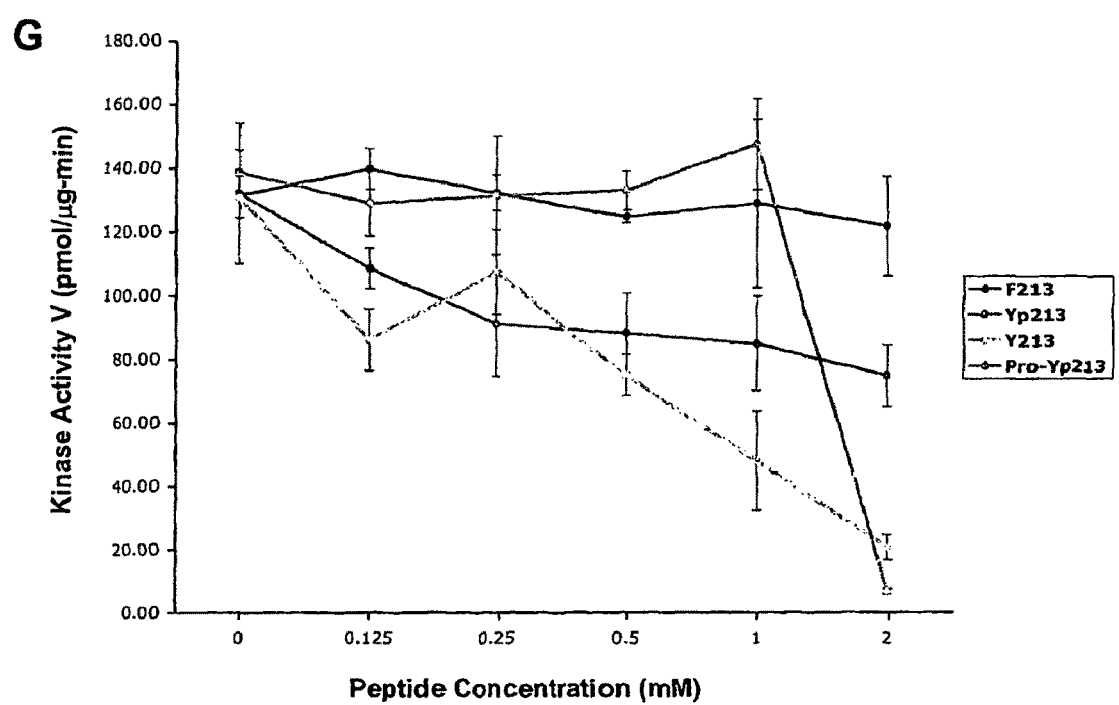
FIG. 3 is graphs of experimental results showing that phosphopeptides from Abi1 regulate c-AbI kinase activity in vitro. Panel A shows kinase activities of c-AbI after addition of indicated peptides at 2 mM. Vertical bars represent±s.d.; n=3. The activities were measured with 5-min kinase assays in the presence of increasing substrate peptide concentrations. Panel B shows double reciprocal Lineweaver-Burke plots of the data in A. Vertical bars represent ±s.d. (n=3). Panel E shows kinase activities (mean±sem; n=3) of c-AbI after addition of Y213 (nonphosphorylated) peptide at indicated concentrations. Panel F shows double reciprocal Lineweaver-Burke plots of the data in Panel E, except for the 2 mM concentration. See Table 2 for $V_{max}$ and $K_m$ data from these experiments. Panels C, D and G show c-AbI kinase activity following addition of peptides from Abi1 (FIG. 1A) at 100 μM of substrate peptide, PEP; concentration of Abi1 peptides as indicated; vertical bars represent s.e.m. (n=3). Panel G is the same as C but contains additional data from Y213 experiments. See FIG. 1A for sequence information of peptides used here.

The proximity of the AbI SH3 binding site to tyrosine 213 suggests that the phosphorylated tyrosine interacts with AbI SH2 domain. This interaction was analyzed using biotinylated 14-residue peptide containing phosphorylated tyrosine 213 (pY213) and GST-AbI SH2 domain fusion protein (FIGS. 2B-D). First, it was established that the AbI SH2 domain interacts with the phosphopeptide pY213 but not with the nonphosphopeptide Y213 (FIG. 2B). Using varying concentration of AbI SH2 domain we determined that pY213 interacts with the SH2 domain with high affinity (association constant, $K_A$=3.01×10⁷; dissociation constant, $K_D$=3.32× 10⁻⁸; association rate, $K_{on}$=1.13×10⁵ s⁻¹; dissociation rate, $K_{off}$=3.76×10⁻³ M⁻¹ s⁻¹) (FIG. 2C). Control experiments showed that the AbI SH2 R171K mutant did not interact with pY213 (FIG. 2D) consistent with the finding that the R171 mutation renders SH2 domain incapable for interaction with phosphopeptides (Mayer et al., 1992).

pY213 phosphoeptide inhibits c-AbI kinase activity by a noncompetitive mechanism. Based on the crystal structure of c-AbI kinase, SH2 domain-phosphopeptide interaction has the potential to regulate c-AbI kinase activity (Hantschel et al., 2003). Therefore experiments were performed to test whether the sequences of Abi containing tyrosine 213 affect c-AbI kinase activity. In these experiments, active c-AbI (Tanis et al., 2003), the model substrate peptide (Brasher and Van Etten, 2000; Pluk et al., 2002), and forms of the 14-residue peptide containing phosphotyrosine, pY213, or tyrosine to phenylalanine replacement at position 213, F213 (for peptide sequences see FIG. 1A) were used. The pY213 phosphopeptide showed 38% reduction of $V_{max}$ and no significant effect on $K_m$ of the substrate peptide consistent with the noncompetitive mechanism of inhibition (FIGS. 3A-B, and Table 2). No effect on the kinase activity was observed with the peptide F213.

TABLE 2

Kinetic analysis of Abi1 peptides

| Peptide | $V_{max}$ (pmol/min-μg) | Fold Change (PEP) | $K_m$ (μM) |
|---|---|---|---|
| PEP | 157.79 ± 9.29 | 1.00 | 21.19 ± 3.37 |
| F213 | 163.08 ± 17.90 | 1.03 | 25.79 ± 5.56 |
| pY213 | 97.51 ± 9.17** | 0.62 | 24.90 ± 5.63 |
| Y213 - 0.1 | 112.11 ± 7.80* | 0.71 | 14.89 ± 2.74* |
| Y213 - 0.25 | 86.68 ± 19.71* | 0.55 | 16.52 ± 7.29 |
| Y213 - 2.0 | 2.90 ± 1.16* | 0.018 | 16.28 ± 0.60* |

Summary of $V_{max}$ and $K_m$ (mean ± s.d.; n = 3) for Abi1 peptides at 2 mM for F213 and pY213.
*p ≤ 0.05;
**p ≤ 0.001;
PEP, substrate peptide. For description of peptides see FIG. 1A.

The nonphosphorylated peptide Y213 demonstrated a more significant reduction of the kinase activity than pY213 at 2 mM (Table 2). It also demonstrated significant kinase inhibition at lower concentrations than the pY213 peptide (FIGS. 3E and 3F, and Table 2). The 14-residue peptide Y213 may act as a substrate for AbI kinase itself and it competed with the model substrate peptide. However, the Lineweaver-Burke curve showed a decrease of $K_m$ of the substrate peptide (significant at 0.1 mM and 2.0 mM of Y213 peptide concentration, Table 2) and lower $V_{max}$ thus suggesting inhibition of kinase activity by lowering turnover of the substrate peptide. Interestingly, inclusion of the SH3 domain binding sequence at the N-terminus of the pY213 phosphopeptide enhanced the inhibitory effect on c-AbI kinase at a peptide concentration of 2 mM, but no inhibition was observed at lower concentrations (FIG. 3G). In summary, with the exception of Y213F, all peptide 14-mers tested, i.e. pY213, and Y213, as well as the 49-mer, ProYp213, showed inhibition of c-AbI kinase activity. However, the mechanism of inhibition may be different with different peptides.

SH3 domain binding is critical for inhibition of c-AbI kinase activity. Inclusion of the SH3 domain binding sequence containing $^{181}$PPSPP$^{185}$ at the N-terminus of the pY213 phosphopeptide (peptide Pro-pY213) enhanced the inhibitory effect on c-AbI kinase at a peptide concentration of 2 mM, but no inhibition was observed at lower concentrations (FIG. 3C). In fact, c-AbI kinase showed some increase in activity between 0.5 and 1 mM. To learn more about this effect the kinase activity was examined using peptides derived from Pro-pY213 containing the sequences N-terminal to pY213 (FIG. 3D). Peptide Pro-Y198 showed increased inhibition with increasing peptide concentrations; this effect was lost with mutations of the SH3 binding motif $^{181}$PPSPP$^{185}$ to $^{181}$PESEP$^{185}$ (peptide EE-Y198) or with the Y198 to F198 replacement (peptide Pro-F198). Peptide Pro-pY213 increased the kinase activity at concentrations from 0.75 to 1.25 mM, which was followed by the decrease of activity at 1.5 mM and inhibition at 1.75 and 2 mM. These data indicate that: (a) Pro-pY213 is capable of up-regulating or down-regulating c-AbI activity depending on the concentration; and (b) the sequences $^{181}$PPSPP$^{185}$, and pY213 of Abi1 are critical for the regulation of c-AbI kinase activity by Pro-pY213.

Abi1 Y213 is phosphorylated in c-AbI dependent manner. To determine whether tyrosine 213 is phosphorylated in vivo cultured cell lines were used as model systems. Experiments in AbI-/-Arg-/- double knockout cells using the phospho-specific antibody indicate that Y213 is phosphorylated only when Abi1 is co-transfected with c-AbI kinase (FIG. 4A). Remarkably, the mutation Y213F led to an apparent decreased stability of Abil-F213 when co-transfected with c-AbI (FIG. 4A). Lower stability of Abi1-ΔEx6 upon co-transfection with c-AbI was also apparent, although the recombinant band overlaps with the IgG band. No changes in transient transfection efficiencies or in the recombinant protein localizations were observed with either of the Abi1 mutants and they all co-localized with the recombinant c-AbI (data not shown).

Abi1 expression regulates cell proliferation and cell spreading of LnCAP cells by regulating c-AbI kinase activity. To determine whether Abi1 regulates c-AbI tyrosine kinase activity in cells the LnCAP prostate cancer cell line was used as a model system. The LnCAP cell line contains a heterozygous, exon 6-skipping mutation, resulting in the loss of Abi1 region containing Y213 (Macoska et al., 2001). This leads to an apparent low-level expression of Abi1 in LnCAP cells (see FIG. 9). Consistent with established functions of c-AbI kinase, stable cell lines supplemented with Abi1-wt showed growth inhibition (FIG. 5A) and decreased cell spreading activity (FIGS. 5B-C). Using the same assay we showed that STI-571 has similar inhibitory effect on cell spreading activity of LnCAP cells as expression of Abi1 (FIG. 5C). c-AbI activity was significantly reduced in Abi1-transfected LnCAP cells (FIG. 6) despite the fact that only a small increase of total Abi1 expression was observed (FIG. 6A). c-AbI showed reduced activity as indicated by the reduced phosphorylation of exogenous Crk substrate or endogenous Crk (FIG. 6B), as well as the reduced tyrosine phosphophorylation of the 8E9 immunoreactive band (FIG. 6C). Phosphorylation of the activation loop tyrosine Y412 of c-AbI was also reduced. These were accompanied by reduced tyrosine phosphorylation of protein lysates in LnCAP cells. These data clearly indicate lower activity of c-AbI in Abi1 transfected cells. Thus increased levels of Abi1 in Abi1(+) cells line led to decreased cell growth and cell spreading by down-regulating c-AbI activity. The fact that Abi1 co-precipitated with c-AbI more efficiently in LnCAP cells, where tyrosine 213 is more phosphorylated due to an increased activity of c-AbI, than from Abi1(+) cells (FIG. 6D), supports negative feedback mechanism of c-AbI inhibition by its substrate i.e. Abi1.

Abi1's pY213 and $^{181}$PPSPP$^{185}$ sequences regulate c-AbI tyrosine kinase activity and couple it to the regulation of cell proliferation and cell spreading. To circumvent an apparent low stability of Abi1-F213 in transient transfections and to specifically address the roles of Abi1 's pY213 and $^{181}$PPSPP$^{185}$ in c-AbI kinase activity and in cell proliferation LnCAP clones were obtained that were stably transfected with the wild type, Abi1-wt, or with the following mutants of Abi1: Y213F, Abi1-Y213F, and $^{181}$PPSPP$^{185}$ to $^{181}$AESEA$^{185}$ and Abi1-Pro. Expression of Abi1 -F213 did not inhibit c-AbI kinase activity, nor did the expression of Abi1-Pro (FIGS. 7A and 7B) in contrast to Abi1-wt as examined by levels of phosphorylation of the activation loop tyrosine (pY412) or by levels of endogenous Crk phosphorylation. Thus inhibition of c-AbI kinase by the negative feedback mechanism does not take place in Abi1-F213 cells even though higher levels of the inhibitor are expressed in these cells than in Abi1 -wt cells. Analysis of growth rates of Abi1 clones indicated that these rates were higher in cells with higher c-AbI kinase activity (FIG. 7C) with the exception of Abi1-Y213F clones that proliferated with the slowest rate and were similar to Abi1(+) and Abi1-wt clones but in contrast had high c-Abl activity. Cell spreading activity of Abi1 clones on collagen was also evaluated. Only cells expressing the wild type Abi1 i.e. clones Abi1(+) and Abi1 -wt showed decreased cell spreading (FIG. 7D). These cells had lower c-Abl kinase activity thus cell spreading activity of LnCAP cells is regulated by the Abi1-dependent c-Abl tyrosine kinase activity. Interestingly, high cell spreading activity of cells was independent from the growth signal of Abi1 i.e. Abi1-F213 clones showed similar cell spreading activity to Abi1-Pro clones, but they grew significantly slower).

Discussion

A plausible mechanism is provided by which Abi1 regulates c-Abl tyrosine kinase activity. The mechanism involves phosphorylation of Y213 in the N-terminal region of Abi1 by c-Abl kinase, followed by its binding to the Abl SH2 domain and leading to subsequent inhibition of the kinase. This is the first demonstration of c-Abl kinase inhibition by a phosphopeptide located in trans in another protein, namely Abi1. The phosphorylation of Abi1 at Y213 by c-Abl kinase has not previously been demonstrated although it has been identified as the phosphorylation site for BCR-Abl in a shogun approach to determine STI-571 dependent substrate targets of BCR-Abl (Goss et al., 2006).

Abi1 phosphopeptides inhibit c-Abl kinase through an allosteric mechanism. This mechanism involves high affinity binding of the phosphorylated Y213 to the Abl SH2 domain. An observed decrease of the $V_{max}$, with no change of the $K_m$ is consistent with a noncompetitive mechanism of inhibition of kinase activity by the phosphopeptide containing pY213. Structural studies of c-Abl (Hantschel et al., 2003; Nagar et al., 2003) indicate that the phosphotyrosine binding site is partially occluded in the crystal structure of the nonmyristoylated c-Abl fragment containing the SH3-SH2-catalytic domain assembly. In vitro kinase data that was obtained pertains to the nonmyristoylated, uncapped c-Abl kinase that is shared by both 1a and 1b forms of the kinase. Thus, interaction with the Abi1 phosphopeptide pY213 must involve significant conformational change in the c-Abl molecule (specifically of the SH2 and kinase domains).

Molecular modeling indicates that Abi1 stabilizes the inactive kinase conformation. See FIG. 8A). This conformation may be similar to one observed in myristoylated kinase, or to that proposed to be stabilized by GNF-2 binding to the myristoyl-binding pocket (Adrian et al., 2006). In the myristate-bound state, the inactive kinase conformation is achieved by specific positioning of the C-terminal αI' helix of the kinase domain (Hantschel et al., 2003; Nagar et al., 2003). This further reinforces the autoinhibitory assembly of the SH3, SH2 and CD domains It is conceivable that Abi1 binding to c-Abl kinase may enforce an inhibitory conformation of Abl kinase by affecting the positioning of C-terminal helix in the C-lobe of Abl catalytic domain. This is due to stabilization of the SH2 domain-catalytic domain interaction by the Abi1 phosphopeptide as supported by the molecular modeling data (FIG. 8A). Abi1-binding to BCR-Abl might explain why small molecules such as GNF-2, which is hypothesized to act like myristoyl group by stabilizing the bent αI' helix conformation (FIG. 8B), inhibits BCR-Abl in cells (Adrian et al., 2006).

The binding to the Abl SH3 domain is critical in regulation of c-Abl kinase activity by Abi1. This is demonstrated by the regulation of kinase activities by the phosphopeptide Pro-pY213 that includes both the Abl SH2 and Abl SH3 domain binding regions of Abi1. Pro-pY213 elicits both up-regulating and down-regulating effects on the kinase activity, which depend on the peptide concentration. At lower concentrations Pro-pY213 upregulates Abl activity; this is most likely by competing with and alleviating the inhibitory interactions of SH3 and SH2 domains with the catalytic domain (CD) and SH2-catalytic domain linker (Brasher et al., 2001; Nagar et al., 2003). These data suggest steps in c-Abl activation by Pro-pY213 involving uncoupling of SH3 and SH2 domains from the CD domain as observed recently in c-Src (Cowan-Jacob et al., 2005) or as suggested by SAXS analysis of active c-Abl (Nagar et al., 2006). Further analysis of peptides derived from the N-terminal region of Pro-pY213 indicates that the SH3-binding sequence, $^{181}$PPSPP$^{185}$, and Y198 are important for the regulation of c-Abl kinase; this is most likely by stabilizing the inhibited conformation of the kinase. Up-regulation of the kinase activity can be only observed with the full-length Pro-pY213 peptide thus all three elements of the peptide PPSPP, Y198, and pY213 are necessary to elicit this effect. At higher concentrations Pro-pY213 is likely to fully engage in interactions with all three c-Abl domains i.e. SH3, SH2, and CD likely resulting in stabilization of a new inhibited conformation of the kinase (FIG. 8A). Using Biacore, it was determined that GST-SH3-SH2 interacts with and pY213 with a Kd very similar to that observed with GST-SH2 and Pro-pY213, in the low millimolar range (data not shown). These and the structural data relating to the role of phosphoserine 69 suggest that SH3 and SH2 domains are quite disordered in the GST-SH3-SH2. Therefore, a high concentration of Pro-pY213 is necessary to stabilize its interaction with the SH3-SH2 domains in vitro. This may also explain why quite high concentrations of the Pro-pY213 peptide are needed to elicit the effect on c-Abl activity in vitro kinase assays. However, the recent c-Abl structure indicates that the interaction of Abl SH3 and SH2 domains are stabilized by phosphoserine 69 suggesting that these domains may act as one unit in the assembled structure (Nagar et al., 2006). In this model of c-Abl kinase regulation by Abi1, which incorporates the current structural information about c-Abl (Hantschel et al., 2003; Nagar et al., 2003; Nagar et al., 2006), it is proposed that Pro-pY213 first opens up the autoinhibited structure, leading to an elongated more active Abl (as proposed by SAXS analysis, (Nagar et al., 2006); this followed by less active and inactive intermediates, with partially or fully closed structures (FIG. 8B).

Previously, Hantschel et al, 2003 (Hantschel et al., 2003) demonstrated that short phosphotyrosine-containing peptides can activate myristoylated c-Abl kinase. Such phosphopeptides, possibly representative of growth factor receptor cytoplasmic domains in vivo, may activate c-Abl kinase by competing with the inhibitory protein Abi1 for binding to Abl's phosphotyrosine-binding site.

The peptide Y213 that contains the substrate tyrosine 213 showed the most potent inhibition of Abl kinase activity. The Km decreases of the substrate peptide as well as the decreases of Vmax (at 0.1 mM and 2 mM) suggest that the Y213 peptide may decrease turnover of other Abl substrates. This may have physiological significance since the Abi1/Hssh3bpl targets other cellular substrates to Abl kinase (Maruoka et al 2005).

Experiments in LnCAP cells confirm the mechanism of c-Abl regulation by SH3 and SH2 binding to Abi1. Expression of Abi1 with mutations in the Abl SH2 domain (Y213F) or in the SH3 domain (181PPSPP185) binding sequences, $^{181}$PPSPP$^{185}$, leads to decreased ability of Abi1 to inhibit c-Abl. In cells stably transfected with Abi1 mutants, higher c-Abl activity was observed, as measured by phosphorylation of the activation loop tyrosine pY412 of c-Abl as well as by the enhanced tyrosine phosphorylation of its substrate Crk. Lower c-Abl kinase activity as a result of the negative feedback inhibition upon expression of wild type Abi1 in LnCAP cells is consistent with the down-regulation of c-Abl role in mitogenic effects downstream from growth factors receptors such as PDGF or integrin signaling (Wang, 2004; Woodring et al., 2002). Consequently, lower c-AbI kinase activity leads to inhibition of cell proliferation and cell spreading activity. Previously, c-AbI kinase activity was linked to increased integrin signaling (Lewis et al., 1996), microspike formation (Woodring et al., 2002; Stuart et al, 2006), or cell spreading (Leng et al., 2005) however no clear mechanism in the process was proposed for Abi1.

The fact that Abi1 -Pro clones proliferated with the fastest rate, have high AbI tyrosine kinase activity, and that they contain Y213 suggest that Y213 and/or more likely pY213 may play a role in transmitting the growth signal downstream of c-AbI kinase. LnCAP clones transfected with the wild type Abi1 contain higher levels of Y213 (as higher levels of the protein are observed) than wild type LnCAP cells, but have lower c-AbI activity due to the negative feedback by pY213, the product of its phosphorylation substrate Y213. Consistently, Abi1(+) cells grow slower than the wild type LnCAP cells due lower levels of pY213 (see FIG. 6D). This idea is also consistent with the fact that Abi1-F213 cells also grow slowly as the recombinant Abi1-F213 cannot be phosphorylated by on Y213. If pY213 is promoting cell growth, for example by binding to a downstream effector, while also inhibiting c-AbI kinase activity, this would suggest a very tight regulation of c-AbI dependent growth signals by its substrate Abi1, which also acts as c-AbI inhibitor by the negative feedback loop.

Interestingly, cell spreading activity corresponds with high AbI kinase activity in cells; this included Abi1 -F213 cells that exhibit growth inhibition. Thus Abi1 -dependent growth regulation is separated from the Abi1 -dependent regulation of cell spreading. This regulation may involve regulation of phosphorylation of Wave 2. Phosphorylation of Wave 2 by c-AbI has been suggested to promote Arp2/3 and actin cytoskeleton reorganization that regulate cell spreading (Leng et al., 2005; Stuart et al., 2006). Lower expression of Abi1 in wild type LnCAP cells, or expression of Abi1 with mutations that abolish Abi1's inhibitory effect on AbI kinase activity may lead to hyperphosphorylation of Wave 2, which is likely to lead to increased cell spreading of cells. Thus increased cell spreading activity is consistent with high c-AbI tyrosine activity and not with presence of Y213 (in contrast to cell growth) (FIG. 10).

These data suggest a general mechanism of kinase regulation of nonreceptor AbI tyrosine kinases such as c-AbI and Arg by the Abi/Hssh3bpl family of proteins. The Hssh3bpl gene is on chromosome 10p11.2 (Ziemnicka-Kotula et al., 1998), GenBank Accession No. U18766); Hssh3bpl is the human homologue of Abi1 whose partial sequence was first identified in mouse (Shi et al., 1995), the full sequence of mouse Abi1 was reported more recently (Ikeguchi et al., 2001). The region containing the regulatory tyrosine 213 is highly conserved between Abi1 and Abi2 from human down to *Xenopus*, and is present in *Drosophila* Abi (Table 3). The conserved sequences also include the PXXP motif, $^{181}$PPSPP$^{185}$, which binds to the c-AbI SH3 domain, and tyrosine 198. All isoforms of Abi1 or Abi2 identified so far (Ziemnicka-Kotula et al., 1998, and L. Kotula, unpublished data) contain the regulatory sequence indicating the conservation of c-AbI regulation in all Abi isoforms. The conserved region of Abi apparently plays a role in the regulation of c-AbI kinase activity in cells, here we studied the role of the regulatory sequences in isoform 2 of Abi1. The phosphorylation of the regulatory Y213 is followed by the Abi's binding to the AbI SH2 and SH3 domains. This leads to transient up-regulation and subsequent down-regulation of c-AbI kinase activity. This molecular regulation has physiological significance since a number of proteins binding to Abi1 are targeted to c-AbI kinase as substrates for phosphorylation (Leng et al., 2005; Maruoka et al., 2005; Tani et al., 2003). Thus c-AbI kinase must be tightly regulated for the complex containing the Abi protein, c-AbI, and a substrate to turnover following a cycle of phosphorylation. Since Abi1 is also a substrate of c-AbI the proposed regulation suggest a negative feedback mechanism. c-AbI SH3 and SH2 binding to Abi1 is critical for this regulatory mechanism in cells as mutations in these domain result in cellular transformation (Jackson and Baltimore, 1989; Mayer et al., 1992). The Arg kinase, the second member of AbI family, which shares all regulatory domains with c-AbI, as well as similar mechanism of STI-571 inhibition (Tanis et al., 2003), is also likely to be regulated by the proposed mechanism.

TABLE 3

Abi1 and Abi2 sequence comparisons

| | | SEQ ID NO: |
|---|---|---|
| Abi1 | | |
| *Homo sapiens* | $^{178}$TQKPPSPP-MSGRGTLGRNT-PYKTLEPVKPPTVPNDpYMTSP$^{217}$ | 9 |
| *Bos taurus* | $^{178}$TQKPPSPP-VSGRGTLGRNT-PYKTLEPVKPPTVPNDpYMTSP$^{217}$ | 10 |
| *C. familiaris* | $^{178}$TQKPPSPP-VSGRGTLGRNT-PYKTLEPVKPPTVPNDpYMTSP$^{217}$ | 10 |
| *Mus musculus* | $^{178}$TQKPPSPP-VSGRGTLGRNT-PYKTLEPVKPPTVPNDpYMTSP$^{217}$ | 10 |
| *X. laevis* | $^{178}$TQKPPSPP-MPSRGTLGRNT-PYKTLEPVKPPTVPNDpYMTSP$^{217}$ | 11 |
| Abi2 | | |
| *Homo sapiens* | $^{178}$TQKPPSPP-MSGKGTLGRHS-PYRTLEPVRPPVVPNDpYVPSP$^{217}$ | 12 |
| *Mus musculus* | $^{178}$TQKPPSPP-MSGKGTLGRHS-PYRTLEPVRPPVVPNDpYVPSP$^{217}$ | 12 |
| *Gallus gallus* | $^{172}$TQKPPSPP-MSGKGTLGRHS-PYRTLEPVRPPVVPNDpYVPSP$^{211}$ | 12 |
| *X. tropicalis* | $^{172}$TQKPPSPP-MSGKGTLGRHS-PYRTLEPVRPPVVPNDpYVPSP$^{211}$ | 12 |

TABLE 3-continued

Abi1 and Abi2 sequence comparisons

| | | SEQ ID NO: |
|---|---|---|
| Danio rerio | $^{178}$TQKPPSPP-MSGKGTLGRHS-PYRTLEPVRPPVVPNDpYVPSP$^{217}$ | 12 |
| D. melanogaster | $^{199}$TTKPPSPPQMSGTLGKSSRSYRTPPVVNPPQVPSHpY**APSP$^{252}$ | 13 |
| Consensus | TQKPPSPP MSGxGTLGx z PYxTLEP<u>V</u>x<u>PP</u> <u>VPND</u>pY <u>SP</u> | 7 |

Species comparisons of the c-Abl kinase regulatory region of the Abi protein family. The region of Abi1 containing the Abl SH3 domain binding site containing the core PXXP consensus, PPSPP, Y198, and the SH2 domain binding site (underlined, with regulatory phosphotyrosine, pY) is highly conserved during evolution in the Abi protein family. Critical residues are in bold. GenBank Accession numbers for the sequences are the following: for Abi1: Homo sapiens, U87166 and NM_005470; Bos taurus XP_881074.1; Canis familiaris, XP_858231.1; Mus musculus, Q8CBW3; Xenopus laevis, AAH81178.1; Abi2: Homo sapiens, NP_005750.3; Mus musculus, AAH79646.1; Gallus gallus, XP_421962.1; Xenopus tropicalis, NP_001007488.1; Danio rerio, XP_685431.1, Drosophila melanogaster, AAD38382.1
**denotes insertion of the sequence RAGNTGTLGKSVSNT in Drosophila melanogaster.

In summary, the mechanism of AbI kinases regulation was identified, which can be used as new strategy for anti-AbI kinase drug development. Mutated forms of c-AbI kinase are implicated in certain cancers, e.g., BCR AbI is implicated in chronic myelogenous leukemia (CML), and in some forms of acute lymphocytic leukemia (ALL) (Druker et al., 2001a; Goldman and Melo, 2003). Although the use of STI-571 has brought great promise for the treatment of these diseases, some patients are becoming resistant to the drug following long-term treatments. STI-571-resistant mutations are found in AbI SH3 and SH2 domains (Azam et al., 2003) leading to the possibility that in these cases BCR-AbI escapes its regulation by Abi1 (which is already affected by the presence of BCR in the N-terminus and the lack of regulatory cap region). The mechanism described here should directly impact the future studies of BCR-AbI, aiding in the development of novel allosteric compounds for the treatment of CML.

Experimental Procedures

AbI kinase. His-tagged, uncapped active c-AbI, E46 through C-terminus (isoform 1b) (kind gift of Tony Koleske, Yale University, New Haven, Conn.), was produced and purified from baculovirus as described (Tanis et al., 2003) following treatment of insect cells with 30 µM STI-571 (Novartis Pharma AG, Basel, Switzerland) for 48 hrs prior to cell lysis. The expressed protein was affinity purified on nickel-nitriloacetic acid agarose, washed to remove the inhibitor, and subsequently purified by ion-exchange chromatography using a Mono S column (Amersham Biosciences, Piscataway, N.J.). GST fusions of c-AbI SH2 domain wild type and SH2 domain containing the R171K mutation, and mammalian expression plasmid containing c-AbI-GST (isoform 1b, with the GST at the C-terminus) were obtained from Bruce Mayer (University of Connecticut Health Center, Farmington, Conn.).

Abi1 (GenBank Assession No. NM005470 and U87166 (SEQ ID NO:18)). Wild type or mutant Abi1 isoform 2, residue numbering according to (Ziemnicka-Kotula et al., 1998) were expressed from plasmids. The mutant Abi1-ΔEx6, lacking exon 6 of Abi1 (Macoska et al., 2001), was subcloned from LnCAP cells. The mutant Abi1-F213 contains the Y213F replacement. The mutant Abi1-Pro contains the sequence AESEA instead of PPSPP, residues 181-185 of Abi1, which results in the loss of PXXP SH3 binding motif. All Abi1 cDNAs were subcloned into the pEGFP-N2 plasmid (Clontech, Mountain View, Calif.) following removal of GFP-encoding sequences and introduction of HA tag at the C-terminus. For mass spectroscopy (Table 1) or the SH3 binding assay (FIG. 2A) GST fusion proteins of Abi1 were expressed from pGEX-2T plasmid (Amersham Biosciences, Piscataway, N.J.). All expression plasmids were verified by sequencing. In vitro translation of the N-terminus of Abi1 was performed as described (Macoska et al., 2001).

Kinase assay. Measurement of kinase activity was essentially as described in (Tanis et al., 2003), using biotinylated model substrate peptide GGEAIYAAPFKK (SEQ ID NO: 16), (Brasher and Van Etten, 2000; Songyang et al., 1995) and $^{32}$P-γ-ATP. SAM2 streptavidin-coated membrane (Promega Corporation, Madison Wis.) was used to capture the substrate. Kinase assay mixtures contained 50 mM Tris-HCl pH 7.5, 10 mM MgCl$_2$, 1 mM EGTA, 2 mM dithiothreitol, 0.01% Brij 35, and 100 µM ATP, 2 nM AbI kinase, substrate peptides, and Abi1 ligand peptides as indicated. Reactions were carried out for 5 min. at 30° C. To evaluate c-AbI kinase activity in LnCAP cell lines, cells were treated with pervanadate for 10 min. prior to cell lysis, and immunoprecipitates from lysed cells were tested using GST-Crk as substrate.

Peptides and antibodies. All peptides were synthesized at Genemed Synthesis, Inc. (San Francisco, Calif.). Anti-pY213 polyclonal antibody was produced to peptide pY213, affinity purified using the phosphopeptide-specific column followed by purification on the nonphosphopeptide (Y213) column. PY99 antibody was from Santa Cruz Biotechnology (Santa Cruz, Calif.). Polyclonal and monoclonal HA antibodies were from Covance (Berkeley, Calif.) and Roche Diagnostic Corporation (Indianapolis, Ind.). Antibodies to c-AbI used here were 8E9 (BD Biosciences, San Jose, Calif.), K12 (Santa Cruz Biotechnology, Santa Cruz, Calif.), pY412 (Biosource International, Camarillo Calif.); Crk antibodies were from BD Biosciences, San Jose, Calif. (mouse monoclonal); Santa Cruz Biotechnology, Santa Cruz, Calif. (rabbit polyclonal); and Cell Signaling Technology (phospho-Crk pY221). Polyclonal antibody Ab-2 to Abi1 is described (Xu et al., 2000). Monoclonal antibody 7B6 to Abi1 was produced to the recombinant Abi1; the epitope of this antibody is identical to Mab 4E2 (Ziemnicka-Kotula et al., 1998). Antibody to glyceraldehyde-3-phosphate dehydrogenase (GAPDH) was from Imgenex Corporation (San Diego, Calif.); GST antibody was from Zymed (San Francisco, Calif.). Generic antibodies to phosphotyrosine, PY99 and pY350, were from Santa Cruz Biotechnology, Santa Cruz, Calif.

Cell culture and transfections. Cos7 and LnCAP cells (ATCC, Rockville, Md.) were maintained according to ATCC instructions. Single AbI(−/−) knockout fibroblasts (Koleske et al., 1998) were maintained using fetal bovine serum. All cells were transfected with expression plasmids using Lipofectamine Plus Reagent (Invitrogen, Carlsbad, Calif.). All co-transfections of Abi1 with c-AbI were performed with the isoform 1b of c-AbI and isoform 2 of Abi1 (wild type or mutants). At 22 h post-transfection, cells were processed for indirect immunoprecipitation or immunofluorescence as described by Xu et al., 2000. Stable cell lines expressing wild type or HA-tagged or mutants of Abi 1 isoform 2 of were obtained using G418 selection (Invitrogen, Carlsbad, Calif.); expression of the recombinant gene in subcloned cell lines, Abi1(+) clone 1, and Abi1(+), clone 10, was confirmed by sequencing of RT-PCR products obtained using specific primers. Following selection of HA-tagged Abi1 duplicate clones with similar levels of expression of the recombinant protein were chosen for analyses. Following selection of stable clones all experiments in LnCAP cells or its Abi1 (+) subclones were performed without addition of G418. Rates of cell growth were evaluated by counting the number of cells using BD FACSCanto™ Flow Cytometer and Flow-Count™ Fluorospheres Cat. No 7547053-200 as standard (BD Biosciences, San Jose, Calif.).

Immunoprecipitation and western blotting. Cells were treated with 0.1 mM sodium pervanadate, to inhibit phosphatase, prior to cell lysis. Immunoprecipitation was performed as described (Xu et al., 2000). Western blotting and binding assay to quantify Abl SH3 domain binding was performed as described was performed as described (Ziemnicka-Kotula et al., 1998); blots were developed using Supersignal West Pico Chemiluminescence Substrate (Pierce Biotechnology, Rockford, Ill.). Images were acquired using Kodak GL 440 Imaging System and quantified using Kodak 1D Image Analysis Software (Version 3.6.4) directly or from prior exposures to film.

Confocal microscopy. To evaluate cell spreading activities in LnCAP and Abi1-transfected cells lines, live cell observations were performed using 8-chamber culture slides (BD Biosciences, San Jose, Calif.). Cell spreading activity was scored as following: a cell was scored as having spreading activity if it had any extension (positive), or no spreading activity if a cell was round (negative). In control experiments STI-571 was added to media at 3 µM for 24 hrs prior to replating without the compound. Cells were evaluated at indicated time points in four random regions of interest that were followed for 16 h; for each time point or group n>100 cells. Observations were carried out for 16 h following plating using Zeiss 510 META confocal microscope. To determine cells spreading of LnCAP clones on collagen cells were plated on collagen covered dishes (MatTek Corporation Ashland, Mass.) and mean cell area (n=20) was evaluated (ImageJ, version 1.36b, National Institutes of Health, USA) for each clone 6 hr following the replate.

Surface Plasmon Resonance Assay. Surface plasmon resonance assay was performed using a Biacore 3000 instrument (BIAcore Inc., Piscataway, N.J.). Biotinylated 14-residue peptides, pY213 or Y213, were coupled to surface of streptavidin-coated (SA) biosensor chip (BIAcore Inc., Piscataway, N.J.). Binding reactions were done in HBS-EP buffer, containing 10 mM HEPES, pH 7.4, 150 mM NaCl, 3 mM EDTA, and 0.05% (v/v) surfactant P20. The surface was regenerated before each new injection using 50 mM NaOH and 1M NaCl. The Biacore instrument was programmed to perform a series of binding assays with increasing concentrations of GST Abl SH2 polypeptide over the same regenerated surface. Sensograms (plots of changes in response unit on the surface as a function of time) derived were analyzed using the software BIAeval 3.0. Affinity constants were estimated by curve fitting using a 1:1 binding model.

Molecular Modeling. A twelve-residue phosphotyrosine containing peptide from Abi1 (P206-P217) was modeled based on the x-ray crystal structure of the C-terminal region (F520-E531) of the c-Src protein (pdb entry 2src). Since c-Abl and c-Src kinases have high degree of structural homology and the phosphotyrosine residue (pY) 527 of the c-SRC binds to SH2 domain, the peptide (F520-E531) was placed on the c-Abl x-ray structure (pdb entry 1opl) by aligning two structures in Quanta2000 software (Accelrys, San Diego, Calif.) and by merging the c-Abl and the peptide from the c-SRC protein. This peptide was then mutated to the Abi1 (P206-P217) peptide using the mutagenesis feature in the Triton software, which was designed for in silico construction of protein mutants (Dambosky et al., 2001). Triton uses an external program, Modeller, to generate the three-dimensional structure of the mutants (Fiser and Sali, 2003). Since TRITON does not recognize the phoshotyrosine residue, it was initially replaced with tyrosine. The tyrosine residue, after TRITON mutagenesis run, was mutated backed to the phosphotyrosine residue in Quanta2000. The residue was further modeled using the "Model side chains" within the Protein Design option in Quanta. The Protein Health Check of the mutated peptide docked on c-Abl structure revealed few close contacts and high Charmm energy. The structure was minimized by 50 steps of Steepest Descent, and 100 steps Conjugate Gradient methods to remove those close contacts.

Statistical Analysis. All analyses except evaluation of cell growth and cell spreading activity were done using Microsoft Excel 2004 for Mac Version 11.0. For Table 2 (evaluation of $K_m$ and $V_{max}$), and FIGS. 7B and 7D (Abl kinase activity in LnCAP clones, and cell spreading on collagen) two-tailed paired t-test was used. For evaluation of cell spreading activity, FIG. 5C, $\chi^2$ test was used; for evaluation of cell growth, FIG. 7C, two way ANOVA was used (SigmaStat Version 2, Systat Software Inc., Point Richmond, Calif.). For FIG. 6A-C, two-tailed homoscedastic t-test was used.

References

Adrian, F. J., Ding, Q., Sim, T., Velentza, A., Sloan, C., Liu, Y., Zhang, G., Hur, W., Ding, S., Manley, P., et al. (2006). Allosteric inhibitors of Bcr-abl-dependent cell proliferation. Nat Chem Biol 2, 95-102.

Al-Ali, H. K., Heinrich, M. C., Lange, T., Krahl, R., Mueller, M., Muller, C., Niederwieser, D., Druker, B. J., and Deininger, M. W. (2004). High incidence of BCR-ABL kinase domain mutations and absence of mutations of the PDGFR and KIT activation loops in CML patients with secondary resistance to imatinib. Hematol J 5, 55-60.

Azam, M., Latek, R. R., and Daley, G. Q. (2003). Mechanisms of autoinhibition and STI-571/imatinib resistance revealed by mutagenesis of BCR-ABL. Cell 112, 831-843.

Biesova, Z., Piccoli, C., and Wong, W. T. (1997). Isolation and characterization of e3B1, an eps8 binding protein that regulates cell growth. Oncogene 14, 233-241.

Brasher, B. B., Roumiantsev, S., and Van Etten, R. A. (2001). Mutational analysis of the regulatory function of the c-Abl Src homology 3 domain. Oncogene 20, 7744-7752.

Brasher, B. B., and Van Etten, R. A. (2000). c-Abl has high intrinsic tyrosine kinase activity that is stimulated by mutation of the Src homology 3 domain and by autophosphorylation at two distinct regulatory tyrosines. J Biol Chem 275, 35631-35637.

Buchdunger, E., Zimmermann, J., Mett, H., Meyer, T., Muller, M., Druker, B. J., and Lydon, N. B. (1996). Inhibition of the Abl protein-tyrosine kinase in vitro and in vivo by a 2-phenylaminopyrimidine derivative. Cancer Res 56, 100-104.

Courtneidge, S. A. (2003). Cancer: Escape from inhibition. Nature 422, 827-828.

Cowan-Jacob, S. W., Fendrich, G., Manley, P. W., Jahnke, W., Fabbro, D., Liebetanz, J., and Meyer, T. (2005). The crystal structure of a c-Src complex in an active conformation suggests possible steps in c-Src activation. Structure (Camb) 13, 861-871.

Dai, Z., and Pendergast, A. M. (1995). Abi-2, a novel SH3-containing protein interacts with the c-Abl tyrosine kinase and modulates c-Abl transforming activity. Genes Dev 9, 2569-2582.

Dambosky, J., Prokop, M., and Koca, J. (2001). TRITON: graphic software for rational engineering of enzymes. Trends Biochem Sci 26, 71-73.

Druker, B. J., Sawyers, C. L., Capdeville, R., Ford, J. M., Baccarani, M., and Goldman, J. M. (2001a). Chronic myelogenous leukemia. Hematology (Am Soc Hematol Educ Program), 87-112.

Druker, B. J., Talpaz, M., Resta, D. J., Peng, B., Buchdunger, E., Ford, J. M., Lydon, N. B., Kantarjian, H., Capdeville, R., Ohno-Jones, S., and Sawyers, C. L. (2001b). Efficacy and safety of a specific inhibitor of the BCR-ABL tyrosine kinase in chronic myeloid leukemia. N Engl J Med 344, 1031-1037.

Druker, B. J., Tamura, S., Buchdunger, K, Ohno, S., Segal, G. M., Fanning, S., Zimmermann, J., and Lydon, N. B. (1996). Effects of a selective inhibitor of the Abl tyrosine kinase on the growth of Bcr-Abl positive cells. Nat Med 2, 561-566.

Fiser, A., and Sali, A. (2003). Modeller: generation and refinement of homology-based protein structure models. Methods Enzymol 374, 461-491.

Garber, K. (2006). The second wave in kinase cancer drugs. Nat Bioteclmol 24, 127-130.

Goldman, J. M., and Melo, J. V. (2003). Chronic myeloid leukemia—advances in biology and new approaches to treatment. N Engl J Med 349, 1451-1464.

Gone, M. E., Mohammed, M., Ellwood, K., Hsu, N., Paquette, R., Rao, P. N., and Sawyers, C. L. (2001). Clinical resistance to STI-571 cancer therapy caused by BCR-ABL gene mutation or amplification. Science 293, 876-880.

Goss, V. L., Lee, K. A., Moritz, A., Nardone, J., Spek, E. J., MacNeill, J., Rush, J., Comb, M. J., Polakiewicz, R. D (2006). A common phosphotyrosine signature for the Bcr-Abl kinase. Blood 107, 4888-97.

Hantschel, O., Nagar, B., Guettler, S., Kretzschmar, J., Dorey, K., Kuriyan, J., and Superti-Furga, G. (2003). A myristoyl/phosphotyrosine switch regulates c-Abl. Cell 112, 845-857.

Hantschel, O., and Superti-Furga, G. (2004). Regulation of the c-Abl and Bcr-Abl tyrosine kinases. Nat Rev Mol Cell Biol 5, 33-44.

Ikeguchi, A., Yang, H. Y., Gao, G., and Goff, S. P. (2001) Inhibition of v-Abl transformation in 3T3 cells overexpressing different forms of the Abelson interactor protein Abi-1. Oncogene 20, 4926-4934.

Jackson, P., and Baltimore, D. (1989). N-terminal mutations activate the leukemogenic potential of the myristoylated form of c-abl. Embo J 8, 449-456.

Khorashad, J. S., Anand, M., Marin, D. Saunders, S., Al-Jabary, T., Iqbal, A., Margerison, S., Melo, J. V., Goldman, J. M., Apperley, J. F., and Kaeda, J. (2006). The presence of a BCR-ABL mutant allele in CML does not always explain clinical resistance to imatinib. Leukemia.

Koleske, A. J., Gifford, A. M., Scott, M. L., Nee, M., Bronson, R. T., Miczek, K. A., and Baltimore, D. (1998). Essential roles for the Abl and Arg tyrosine kinases in neurulation. Neuron 21, 1259-1272.

Leng, Y., Zhang, J., Badour, K., Arpaia, E., Freeman, S., Cheung, P., Siu, M., and Siminovitch, K. (2005). Abelson-interactor-1 promotes WAVE2 membrane translocation and Abelson-mediated tyrosine phosphorylation required for WAVE2 activation. Proc Natl Acad Sci USA 102, 1098-1103.

Lewis, J. M., Baskaran, R., Taagepera, S., Schwartz, M. A., and Wang, J. Y. (1996). Integrin regulation of c-Abl tyrosine kinase activity and cytoplasmic-nuclear transport. Proc Natl Acad Sci USA 93, 15174-15179.

Macoska, J. A., Xu, J., Ziemnicka, D., Schwab, T. S., Rubin, M. A., and Kotula, L. (2001). Loss of expression of human spectrin src homology domain binding protein 1 is associated with 10p loss in human prostatic adenocarcinoma. Neoplasia 3, 99-104.

Maruoka, M., Suzuki, J., Kawata, S., Yoshida, K., Hirao, N., Sato, S., Goff, S. P., Takeya, T., Tani, K., and Shishido, T. (2005). Identification of B cell adaptor for PI3-kinase (BCAP) as an Abl interactor 1-regulated substrate of Abl kinases. FEBS Lett 579, 2986-2990.

Mayer, B. J., Jackson, P. K., Van Etten, R. A., and Baltimore, D. (1992). Point mutations in the abl SH2 domain coordinately impair phosphotyrosine binding in vitro and transforming activity in vivo. Mol Cell Biol 12, 609-618.

Miething, C., Feihl, S., Mugler, C., Grundler, R., von Bubnoff, N., Lordick, F., Peschel, C., and Duyster, J. (2006). The Bcr-Abl mutations T315I and Y253H do not confer a growth advantage in the absence of imatinib. Leukemia.

Nagar, B., Hantschel, O., Seeliger, M., Davies, J. M., Weis, W. I., Superti-Furga, G., and Kuriyan, J. (2006). Organization of the SH3-SH2 unit in active and inactive forms of the c-Abl tyrosine kinase. Mol Cell 21, 787-798.

Nagar, B., Hantschel, O., Young, M. A., Scheffzek, K., Veach, D., Bornmann, W., Clarkson, B., Superti-Furga, G., and Kuriyan, J. (2003). Structural basis for the autoinhibition of c-Abl tyrosine kinase. Cell 112, 859-871.

O'Hare, T., Walters, D. K., Deininger, M. W., and Druker, B. J. (2005). AMN107: tightening the grip of imatinib. Cancer Cell 7, 117-119.

Pluk, H., Dorey, K., and Superti-Furga, G. (2002). Autoinhibition of c-Abl. Cell 108, 247-259.

Schindler, T., Bornmann, W., Pellicena, P., Miller, W. T., Clarkson, B., and Kuriyan, J. (2000). Structural mechanism for STI-571 inhibition of abelson tyrosine kinase. Science 289, 1938-1942.

Shah, N. P., Tran, C., Lee, F. Y., Chen, P., Norris, D., and Sawyers, C. L. (2004). Overriding imatinib resistance with a novel ABL kinase inhibitor. Science 305, 399-401.

Shi, Y., Alin, K, and Goff, S. P. (1995). Abl-interactor-1, a novel SH3 protein binding to the carboxy-terminal portion of the Abl protein, suppresses v-abl transforming activity. Genes Dev 9, 2583-2597.

Songyang, Z., Carraway, K. L., 3rd, Eck, M. J., Harrison, S. C., Feldman, R. A., Mohammadi, M., Schlessinger, J., Hubbard, S. R., Smith, D. P., Eng, C., and et al. (1995). Catalytic specificity of protein-tyrosine kinases is critical for selective signalling. Nature 373, 536-539.

Stuart, J. R., Gonzalez, F. H., Kawai, H., Yuan, Z. M. (2006) c-Abl interacts with the WAVE2 signaling complex to induce membrane ruffling and cell spreading. J Biol Chem 281, 31290-7.

Tani, K., Sato, S., Sukezane, T., Kojima, H., Hirose, H., Hanafusa, H., and Shishido, T. (2003). Abl interactor 1 promotes tyrosine 296 phosphorylation of mammalian enabled (Mena) by c-Abl kinase. J Biol Chem 278, 21685-21692.

Tanis, K. Q., Veach, D., Duewel, H. S., Bornmann, W. G., and Koleske, A. J. (2003). Two distinct phosphorylation pathways have additive effects on Abl family kinase activation. Mol Cell Biol 23, 3884-3896.

Thomas, S. M., and Brugge, J. S. (1997). Cellular functions regulated by Src family kinases. Arum Rev Cell Dev Biol 13, 513-609.

von Bubnoff, N., Schneller, F., Peschel, C., and Duyster, J. (2002). BCR-ABL gene mutations in relation to clinical resistance of Philadelphia-chromosome-positive leukaemia to ST1571: a prospective study. Lancet 359, 487-491.

Wang, J. Y. (2004). Controlling AbI: auto-inhibition and co-inhibition? Nat Cell Biol 6, 3-7.

Weisberg, E., Manley, P. W., Breitenstein, W., Bruggen, J., Cowan-Jacob, S. W., Ray, A., Huntly, B., Fabbro, D., Fendrich, G., Hall-Meyers, E., et al. (2005). Characterization of AMN107, a selective inhibitor of native and mutant Bcr-AbI. Cancer Cell 7, 129-141.

Williams, J. C., Weijland, A., Gonfloni, S., Thompson, A., Courtneidge, S. A., Superti-Furga, G., and Wierenga, R. K. (1997). The 2.35 A crystal structure of the inactivated form of chicken Src: a dynamic molecule with multiple regulatory interactions. J Mol Biol 274, 757-775.

Woodring, P. J., Hunter, T., and Wang, J. Y. (2003). Regulation of F-actin-dependent processes by the AbI family of tyrosine kinases. J Cell Sci 116, 2613-2626.

Woodring, P. J., Litwack, E. D., O'Leary, D. D., Lucero, G. R., Wang, J. Y., and Hunter, T. (2002). Modulation of the F-actin cytoskeleton by c-AbI tyrosine kinase in cell spreading and neurite extension. J Cell Biol 156, 879-892.

Xu, J., Ziemnicka, D., Merz, G. S., and Kotula, L. (2000). Human spectrin Src homology 3 domain binding protein 1 regulates macropinocytosis in NIH 3T3 cells. J Cell Sci 113 Pt 21, 3805-3814.

Xu, W., Doshi, A., Lei, M., Eck, M. J., and Harrison, S. C. (1999). Crystal structures of c-Src reveal features of its auto-inhibitory mechanism. Mol Cell 3, 629-638.

Ziemnicka-Kotula, D., Xu, J., Gu, H., Potempska, A., Kim, K. S., Jenkins, E. C., Trenkner, E., and Kotula, L. (1998). Identification of a candidate human spectrin Src homology 3 domain-binding protein suggests a general mechanism of association of tyrosine kinases with the spectrin-based membrane skeleton. J Biol Chem 273, 13681-13692.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NO: s

SEQ ID NO: 1-Consensus combination of amino acid SEQ ID NO: 5 and SEQ ID NO: 6. "(a/b)" means the amino acid residue at the indicated position can be a or b.

v(r/k)pp(t/v)vpndy(m/v)(t/p)sp

SEQ ID NO: 2-Human Abi1 amino acid sequence-GenBank NP005461 = NM005470.2.
The SEQ ID NO: 5 14mer is underlined.

```
  1 maelqmllee eipsgkrali esyqnltrva dycennyiqa tdkrkaleet kayttqslas
 61 vayqinalan nvlqlldiqa sqlrrmessi nhisqtvdih kekvarreig ilttnkntsr
121 thkiiapanm erpvryirkp idytvlddvg hgvkwlkakh gnnqpartgt lsrtnpptqk
181 ppsppmsgrg tlgrntpykt lepvkpptvp ndymtsparl gsqhspgrta slnqrprths
241 gssggsgsre nsgsssigip iavptpsppt igpenisvpp psgappappl apllpvstvi
301 aapgsapgsq ygtmtrqisr hnsttsstss ggyrrtpsvt aqfsaqphvn ggplysqnsi
361 siappppmp qltpqipltg fvarvqenia dsptppppp pddipmfdds pppppppvd
421 yedeeaavvq yndpyadgdp awapknyiek vvaiydytkd kddelsfmeg aiiyvikknd
481 dgwyegvcnr vtglfpgnyv esimhytd
```

SEQ ID NO: 3-Human Abi2 amino acid sequence-GenBank NP005750. The SEQ ID NO: 6 14mer is underlined.

```
  1 maelqmllee eipggrralf drytnierva dycennyiqs adkqraleet kayttqslas
 61 vaylintldn nvlqmldiqa sqlrrmessi nhisqtvdih kekvarreig ilttnkntsr
121 thkiiapanl erpvryirkp idytilddig hgvkvstqnm kmgglprttp ptqkppsppm
181 sgkgtlgrhs pyrtlepvrp pvvpndyvps ptrnmapsqq spvrtasvnq rnrtysssgs
241 sggshpssrs ssrensgsgs vgvpiavptp sppsvfpghp vqfysmnrpa srhtpptigg
301 slpyrrppsi tsqtslqnqm nggpfysgnp vslappppsi lqvtptlplm gfvarvqeni
361 sdtpppppv eepvfdespp ppppedyee eeaavveysd pyaeedppwa prsylekvva
421 iydytkdked elsfqegaii yvikknddgw yegvmngvtg lfpgnyvesi mhyse
```

SEQ ID NO: 4-Human Abi3 amino acid sequence-GenBank AAA75446. The SEQ ID NO: 6 14mer is underlined.

```
  1 messinhisq tvdihkekva rreigilttn kntsrthkii apanlerpvr yirkpidyti
 61 lddighgvkv stqnmkmggl prttpptqkp psppmsgkgt lgrhspyrtl epvrppvpn
121 dyvpsptrnm apsqqspvrt asvnqrnrty stsgssggsh pssrsssren sgsgsvgvpi
181 avptpsppsv fpghpvqfys mnrpasrhtp ptiggslpyr rppsitsqts lqnqmnggpf
241 ysqnpvslap pppsilqvtp qlplmgfvar vqenisdtpp ppppveepvf despppppp
301 edyeeeaavv veysdpyaee dppwaprsyl ekvvaiydyt kdkedelsfq egaiiyvikk
361 nddgwyegvm ngvtglspgn yvesimhyse
```

SEQ ID NO: 5-Fourteen-mer amino acid sequence from Abi1
vkpptvpndymtsp

APPENDIX-continued

SEQ ID NO: s

SEQ ID NO: 6-Fourteen-mer amino acid sequence from Abi2 and Abi3
vrppvvpndyvpsp

SEQ ID NO: 7-The consensus amino acid sequence from Table 3. "(a/b)"
means the amino acid residue at the indicated position can be a or
b. "X" is any amino acid. pY is phosphotyrosine
TQKPPSPPMSG(K/R)GTLG(K/R)X(S/T)PYXTLEPV(K/R)PPXVPNDpYXXSP SEQ ID NO: 8-Forty-nine-mer amino acid sequence from FIG. 1
GTLSRTNPLTQKPPSPPMSGRGTLGRNTPYKTLEPVKPPTVPNDpYMTSP SEQ ID NO: 9-Fragment of Homo sapiens Abi1 amino acid sequence,
from Table 3.
TQKPPSPPMSGRGTLGRNTPYKTLEPVKPPTVPNDpYMTSP SEQ ID NO: 10-Fragment of Bos taurus, Canis familiaris and Mus
musculus Abi1 amino acid sequence, from Table 3.
TQKPPSPPVSGRGTLGRNTPYKTLEPVKPPTVPNDpYMTSP SEQ ID NO: 11-Fragment of Xenopus laevis Abi1 amino acid sequence,
from Table 3.
TQKPPSPPMPSRGTLGRNTPYKTLEPVKPPTVPNDpYMTSP217

SEQ ID NO: 12-Fragment of Homo sapiens, Mus musculus, Gallus gallus,
Xenopus tropicalis and Danio rerio Abi2 amino acid sequence, from
Table 3.
TQKPPSPPMSGKGTLGRHSPYRTLEPVRPPVVPNDpYVPSP SEQ ID NO: 13-Fragment of Drosophila melanogaster Abi2 amino acid
sequence, from Table 3.
TTKPPSPPQMSRAGNTGTLGKSVSNTGTLGKSSRSYRTPPVVNPPQVPSHpYAPSP

What is claimed is:

1. A method of inhibiting an AbI kinase, the method comprising contacting a cell or tissue expressing the AbI kinase with a purified compound selected from the group consisting of SEQ ID NO:1, SEQ ID NO:2, SEQ ID NO:5, SEQ ID NO:6, SEQ ID NO:7, SEQ ID NO:8 and SEQ ID NO:18; and thereby inhibiting the activity of said AbI kinase; wherein said cell or tissue is part of a living mammal that has, or is at risk for, leukemia or prostate cancer.

2. The method of claim 1, wherein the compound consists of SEQ ID NO:1, wherein the tyrosine at residue 10 is phosphorylated.

* * * * *

UNITED STATES PATENT AND TRADEMARK OFFICE
CERTIFICATE OF CORRECTION

PATENT NO.         : 8,148,320 B2                                                           Page 1 of 1
APPLICATION NO.    : 12/095728
DATED              : April 3, 2012
INVENTOR(S)        : Leszek Kotula It is certified that error appears in the above-identified patent and that said Letters Patent is hereby corrected as shown below:

In the Specification

Column 1, lines 12 - 18, remove the text reading "The U.S. Government has a paid-up license in this invention and the right in limited circumstances to require the patent owner to license others on reasonable terms as provided for by the terms of Grant DAMD17-01-1-0096 awarded by The Department of Defense and Grant R01 NS44968 from The National Institute of Neurological Disorders and Stroke." and insert --This invention was made with government support under Grant DAMD17-01-1-0096 awarded by the Department of Defense and Grant R01 NS44968 awarded by the National Institute of Neurological Disorders and Stroke. The government has certain rights in the invention.--.

Signed and Sealed this
Second Day of February, 2016

Michelle K. Lee
*Director of the United States Patent and Trademark Office*

SEQUENCE LISTING

<160> NUMBER OF SEQ ID NOS: 18

<210> SEQ ID NO 1
<211> LENGTH: 14
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X is R or K
<220> FEATURE:
<221> NAME/KEY: MISC_FEATURE
<222> LOCATION: (5)..(5)
<223> OTHER INFORMATION: X is T or V
<220> FEATURE:
<221> NAME/KEY: MISC_FEATURE
<222> LOCATION: (11)..(11)
<223> OTHER INFORMATION: X is M or V
<220> FEATURE:
<221> NAME/KEY: MISC_FEATURE
<222> LOCATION: (12)..(12)
<223> OTHER INFORMATION: X is T or P

<400> SEQUENCE: 1

Val Xaa Pro Pro Xaa Val Pro Asn Asp Tyr Xaa Xaa Ser Pro
1               5                   10

<210> SEQ ID NO 2
<211> LENGTH: 508
<212> TYPE: PRT
<213> ORGANISM: Human

<400> SEQUENCE: 2

```
Met Ala Glu Leu Gln Met Leu Leu Glu Glu Ile Pro Ser Gly Lys
1               5                   10                  15

Arg Ala Leu Ile Glu Ser Tyr Gln Asn Leu Thr Arg Val Ala Asp Tyr
            20                  25                  30

Cys Glu Asn Asn Tyr Ile Gln Ala Thr Asp Lys Arg Lys Ala Leu Glu
                35                  40                  45

Glu Thr Lys Ala Tyr Thr Thr Gln Ser Leu Ala Ser Val Ala Tyr Gln
        50                  55                  60

Ile Asn Ala Leu Ala Asn Asn Val Leu Gln Leu Leu Asp Ile Gln Ala
65                  70                  75                  80

Ser Gln Leu Arg Arg Met Glu Ser Ile Asn His Ile Ser Gln Thr
                85                  90                  95

Val Asp Ile His Lys Glu Lys Val Ala Arg Arg Glu Ile Gly Ile Leu
                100                 105                 110

Thr Thr Asn Lys Asn Thr Ser Arg Thr His Lys Ile Ile Ala Pro Ala
            115                 120                 125

Asn Met Glu Arg Pro Val Arg Tyr Ile Arg Lys Pro Ile Asp Tyr Thr
        130                 135                 140

Val Leu Asp Asp Val Gly His Gly Val Lys Trp Leu Lys Ala Lys His
145                 150                 155                 160

Gly Asn Asn Gln Pro Ala Arg Thr Gly Thr Leu Ser Arg Thr Asn Pro
                165                 170                 175

Pro Thr Gln Lys Pro Ser Pro Pro Met Ser Gly Arg Gly Thr Leu
            180                 185                 190

Gly Arg Asn Thr Pro Tyr Lys Thr Leu Glu Pro Val Lys Pro Pro Thr
        195                 200                 205

Val Pro Asn Asp Tyr Met Thr Ser Pro Ala Arg Leu Gly Ser Gln His
210                 215                 220

Ser Pro Gly Arg Thr Ala Ser Leu Asn Gln Arg Pro Arg Thr His Ser
225                 230                 235                 240

Gly Ser Ser Gly Gly Ser Ser Arg Glu Asn Ser Gly Ser Ser Ser
                245                 250                 255

Ile Gly Ile Pro Ile Ala Val Pro Thr Pro Ser Pro Thr Ile Gly
                260                 265                 270

Pro Glu Asn Ile Ser Val Pro Pro Ser Gly Ala Pro Ala Pro
        275                 280                 285

Pro Leu Ala Pro Leu Leu Pro Val Ser Thr Val Ile Ala Ala Pro Gly
    290                 295                 300

Ser Ala Pro Gly Ser Gln Tyr Gly Thr Met Thr Arg Gln Ile Ser Arg
305                 310                 315                 320

His Asn Ser Thr Thr Ser Ser Thr Ser Ser Gly Gly Tyr Arg Arg Thr
                325                 330                 335

Pro Ser Val Thr Ala Gln Phe Ser Ala Gln Pro His Val Asn Gly Gly
            340                 345                 350

Pro Leu Tyr Ser Gln Asn Ser Ile Ser Ile Ala Pro Pro Pro Pro
        355                 360                 365

Met Pro Gln Leu Thr Pro Gln Ile Pro Leu Thr Gly Phe Val Ala Arg
        370                 375                 380

Val Gln Glu Asn Ile Ala Asp Ser Pro Thr Pro Pro Pro Pro
385                 390                 395                 400

Pro Asp Asp Ile Pro Met Phe Asp Ser Pro Pro Pro Pro Pro
            405                 410                 415

Pro Pro Val Asp Tyr Glu Asp Glu Glu Ala Ala Val Val Gln Tyr Asn
            420                 425                 430
```

```
Asp Pro Tyr Ala Asp Gly Asp Pro Ala Trp Ala Pro Lys Asn Tyr Ile
        435                 440                 445

Glu Lys Val Val Ala Ile Tyr Asp Tyr Thr Lys Asp Lys Asp Asp Glu
    450                 455                 460

Leu Ser Phe Met Glu Gly Ala Ile Ile Tyr Val Ile Lys Lys Asn Asp
465                 470                 475                 480

Asp Gly Trp Tyr Glu Gly Val Cys Asn Arg Val Thr Gly Leu Phe Pro
                485                 490                 495

Gly Asn Tyr Val Glu Ser Ile Met His Tyr Thr Asp
            500                 505

<210> SEQ ID NO 3
<211> LENGTH: 475
<212> TYPE: PRT
<213> ORGANISM: Human

<400> SEQUENCE: 3

Met Ala Glu Leu Gln Met Leu Leu Glu Glu Ile Pro Gly Gly Arg
1               5                   10                  15

Arg Ala Leu Phe Asp Arg Tyr Thr Asn Leu Glu Arg Val Ala Asp Tyr
                20                  25                  30

Cys Glu Asn Asn Tyr Ile Gln Ser Ala Asp Lys Gln Arg Ala Leu Glu
            35                  40                  45

Glu Thr Lys Ala Tyr Thr Thr Gln Ser Leu Ala Ser Val Ala Tyr Leu
    50                  55                  60

Ile Asn Thr Leu Asp Asn Asn Val Leu Gln Met Leu Asp Ile Gln Ala
65                  70                  75                  80

Ser Gln Leu Arg Arg Met Glu Ser Ser Ile Asn His Ile Ser Gln Thr
                85                  90                  95

Val Asp Ile His Lys Glu Lys Val Ala Arg Arg Glu Ile Gly Ile Leu
            100                 105                 110

Thr Thr Asn Lys Asn Thr Ser Arg Thr His Lys Ile Ile Ala Pro Ala
    115                 120                 125

Asn Leu Glu Arg Pro Val Arg Tyr Ile Arg Lys Pro Ile Asp Tyr Thr
130                 135                 140

Ile Leu Asp Asp Ile Gly His Gly Val Lys Val Ser Thr Gln Asn Met
145                 150                 155                 160

Lys Met Gly Gly Leu Pro Arg Thr Thr Pro Thr Gln Lys Pro Pro
                165                 170                 175

Ser Pro Pro Met Ser Gly Lys Gly Thr Leu Gly Arg His Ser Pro Tyr
            180                 185                 190

Arg Thr Leu Glu Pro Tyr Arg Pro Pro Tyr Val Pro Asn Asp Tyr Val
    195                 200                 205

Pro Ser Pro Thr Arg Asn Met Ala Pro Ser Gln Gln Ser Pro Val Arg
210                 215                 220

Thr Ala Ser Val Asn Gln Arg Asn Arg Thr Tyr Ser Ser Ser Gly Ser
225                 230                 235                 240

Ser Gly Gly Ser His Pro Ser Arg Ser Ser Arg Glu Asn Ser
                245                 250                 255

Gly Ser Gly Ser Val Gly Val Pro Ile Ala Val Pro Thr Pro Ser Pro
            260                 265                 270

Pro Ser Val Phe Pro Gly His Pro Val Gln Phe Tyr Ser Met Asn Arg
    275                 280                 285

Pro Ala Ser Arg His Thr Pro Thr Ile Gly Gly Ser Leu Pro Tyr
290                 295                 300
```

```
Arg Arg Pro Pro Ser Ile Thr Ser Gln Thr Ser Leu Gln Asn Gln Met
305                 310                 315                 320

Asn Gly Gly Pro Phe Tyr Ser Gln Asn Pro Val Ser Leu Ala Pro Pro
            325                 330                 335

Pro Pro Ser Ile Leu Gln Val Thr Pro Thr Leu Pro Leu Met Gly Phe
        340                 345                 350

Val Ala Arg Val Gln Glu Asn Ile Ser Asp Thr Pro Pro Pro Pro Pro
            355                 360                 365

Pro Val Glu Glu Pro Val Phe Asp Glu Ser Pro Pro Pro Pro Pro Pro
    370                 375                 380

Pro Glu Asp Tyr Glu Glu Glu Ala Ala Val Val Glu Tyr Ser Asp
385                 390                 395                 400

Pro Tyr Ala Glu Glu Asp Pro Pro Trp Ala Pro Arg Ser Tyr Leu Glu
                405                 410                 415

Lys Val Val Ala Ile Tyr Asp Tyr Thr Lys Asp Lys Glu Asp Glu Leu
            420                 425                 430

Ser Phe Gln Glu Gly Ala Ile Ile Tyr Val Ile Lys Lys Asn Asp Asp
        435                 440                 445

Gly Trp Tyr Glu Gly Val Met Asn Gly Val Thr Gly Leu Phe Pro Gly
    450                 455                 460

Asn Tyr Val Glu Ser Ile Met His Tyr Ser Glu
465                 470                 475

<210> SEQ ID NO 4
<211> LENGTH: 390
<212> TYPE: PRT
<213> ORGANISM: Human

<400> SEQUENCE: 4

Met Glu Ser Ser Ile Asn His Ile Ser Gln Thr Val Asp Ile His Lys
1               5                   10                  15

Glu Lys Val Ala Arg Arg Glu Ile Gly Ile Leu Thr Thr Asn Lys Asn
            20                  25                  30

Thr Ser Arg Thr His Lys Ile Ile Ala Pro Ala Asn Leu Glu Arg Pro
        35                  40                  45

Val Arg Tyr Ile Arg Lys Pro Ile Asp Tyr Thr Ile Leu Asp Asp Ile
    50                  55                  60

Gly His Gly Val Lys Val Ser Thr Gln Asn Met Lys Met Gly Gly Leu
65                  70                  75                  80

Pro Arg Thr Thr Pro Thr Gln Lys Pro Ser Pro Pro Met Ser
                85                  90                  95

Gly Lys Gly Thr Leu Gly Arg His Ser Pro Tyr Arg Thr Leu Glu Pro
            100                 105                 110

Tyr Arg Pro Pro Tyr Val Pro Asn Asp Tyr Val Pro Ser Pro Thr Arg
        115                 120                 125

Asn Met Ala Pro Ser Gln Gln Ser Pro Val Arg Thr Ala Ser Val Asn
    130                 135                 140

Gln Arg Asn Arg Thr Tyr Ser Thr Ser Gly Ser Ser Gly Gly Ser His
145                 150                 155                 160

Pro Ser Ser Arg Ser Ser Arg Glu Asn Ser Gly Ser Gly Ser Val
                165                 170                 175

Gly Val Pro Ile Ala Val Pro Thr Pro Ser Pro Pro Ser Val Phe Pro
            180                 185                 190

Gly His Pro Val Gln Phe Tyr Ser Met Asn Arg Pro Ala Ser Arg His
        195                 200                 205
```

```
Thr Pro Pro Thr Ile Gly Gly Ser Leu Pro Tyr Arg Arg Pro Pro Ser
    210                 215                 220
Ile Thr Ser Gln Thr Ser Leu Gln Asn Gly Met Asn Gly Gly Pro Phe
225                 230                 235                 240
Tyr Ser Gln Asn Pro Val Ser Leu Ala Pro Pro Pro Ser Ile Leu
                245                 250                 255
Gln Val Thr Pro Gln Leu Pro Leu Met Gly Phe Val Ala Arg Val Gln
                260                 265                 270
Glu Asn Ile Ser Asp Thr Pro Pro Pro Pro Val Glu Glu Pro
        275                 280                 285
Val Phe Asp Glu Ser Pro Pro Pro Pro Pro Glu Asp Tyr Glu
    290                 295                 300
Glu Glu Glu Ala Val Val Val Glu Tyr Ser Asp Pro Tyr Ala Glu Glu
305                 310                 315                 320
Asp Pro Pro Trp Ala Pro Arg Ser Tyr Leu Glu Lys Val Val Ala Ile
                325                 330                 335
Tyr Asp Tyr Thr Lys Asp Lys Glu Asp Glu Leu Ser Phe Gln Glu Gly
                340                 345                 350
Ala Ile Ile Tyr Val Ile Lys Lys Asn Asp Asp Gly Trp Tyr Glu Gly
                355                 360                 365
Val Met Asn Gly Val Thr Gly Leu Ser Pro Gly Asn Tyr Val Glu Ser
370                 375                 380
Ile Met His Tyr Ser Glu
385                 390

<210> SEQ ID NO 5
<211> LENGTH: 14
<212> TYPE: PRT
<213> ORGANISM: Human

<400> SEQUENCE: 5

Val Lys Pro Pro Thr Val Pro Asn Asp Tyr Met Thr Ser Pro
1               5                   10

<210> SEQ ID NO 6
<211> LENGTH: 14
<212> TYPE: PRT
<213> ORGANISM: Human

<400> SEQUENCE: 6

Val Arg Pro Pro Val Val Pro Asn Asp Tyr Val Pro Ser Pro
1               5                   10

<210> SEQ ID NO 7
<211> LENGTH: 40
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (12)..(12)
<223> OTHER INFORMATION: X is K or R
<220> FEATURE:
<221> NAME/KEY: MISC_FEATURE
<222> LOCATION: (17)..(17)
<223> OTHER INFORMATION: X is K or R
<220> FEATURE:
<221> NAME/KEY: MISC_FEATURE
<222> LOCATION: (18)..(18)
<223> OTHER INFORMATION: X is any amino acid
<220> FEATURE:
<221> NAME/KEY: MISC_FEATURE
```

```
<222> LOCATION: (19)..(19)
<223> OTHER INFORMATION: X is S or T
<220> FEATURE:
<221> NAME/KEY: MISC_FEATURE
<222> LOCATION: (22)..(22)
<223> OTHER INFORMATION: X is any amino acid
<220> FEATURE:
<221> NAME/KEY: MISC_FEATURE
<222> LOCATION: (28)..(28)
<223> OTHER INFORMATION: X is K or R
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: MISC_FEATURE
<222> LOCATION: (36)..(36)
<223> OTHER INFORMATION: X is phosphotyrosine
<220> FEATURE:
<221> NAME/KEY: MISC_FEATURE
<222> LOCATION: (37)..(38)
<223> OTHER INFORMATION: X is any amino acid

<400> SEQUENCE: 7

Thr Gln Lys Pro Pro Ser Pro Pro Met Ser Gly Xaa Gly Thr Leu Gly
1               5                   10                  15

Xaa Xaa Xaa Pro Tyr Xaa Thr Leu Glu Pro Val Xaa Pro Xaa Val
            20                  25                  30

Pro Asn Asp Xaa Xaa Xaa Ser Pro
        35                  40

<210> SEQ ID NO 8
<211> LENGTH: 49
<212> TYPE: PRT
<213> ORGANISM: Human
<220> FEATURE:
<221> NAME/KEY: MISC_FEATURE
<222> LOCATION: (45)..(45)
<223> OTHER INFORMATION: X is phosphotyrosine

<400> SEQUENCE: 8

Gly Thr Leu Ser Arg Thr Asn Pro Leu Thr Gln Lys Pro Ser Pro
1               5                   10                  15

Pro Met Ser Gly Arg Gly Thr Leu Gly Arg Asn Thr Pro Tyr Lys Thr
            20                  25                  30

Leu Glu Pro Val Lys Pro Pro Thr Val Pro Asn Asp Xaa Met Thr Ser
        35                  40                  45

Pro

<210> SEQ ID NO 9
<211> LENGTH: 40
<212> TYPE: PRT
<213> ORGANISM: Human
<220> FEATURE:
<221> NAME/KEY: MISC_FEATURE
<222> LOCATION: (36)..(36)
<223> OTHER INFORMATION: X is phosphotyrosine

<400> SEQUENCE: 9

Thr Gln Lys Pro Pro Ser Pro Pro Met Ser Gly Arg Gly Thr Leu Gly
1               5                   10                  15

Arg Asn Thr Pro Tyr Lys Thr Leu Glu Pro Val Lys Pro Pro Thr Val
            20                  25                  30

Pro Asn Asp Xaa Met Thr Ser Pro
        35                  40

<210> SEQ ID NO 10
```

```
<211> LENGTH: 40
<212> TYPE: PRT
<213> ORGANISM: Bos taurus
<220> FEATURE:
<221> NAME/KEY: MISC_FEATURE
<222> LOCATION: (36)..(36)
<223> OTHER INFORMATION: X is phosphotyrosine

<400> SEQUENCE: 10

Thr Gln Lys Pro Pro Ser Pro Pro Val Ser Gly Arg Gly Thr Leu Gly
1               5                   10                  15

Arg Asn Thr Pro Tyr Lys Thr Leu Glu Pro Val Lys Pro Pro Thr Val
            20                  25                  30

Pro Asn Asp Xaa Met Thr Ser Pro
        35                  40

<210> SEQ ID NO 11
<211> LENGTH: 40
<212> TYPE: PRT
<213> ORGANISM: Xenopus laevis
<220> FEATURE:
<221> NAME/KEY: MISC_FEATURE
<222> LOCATION: (36)..(36)
<223> OTHER INFORMATION: X is phosphotyrosine

<400> SEQUENCE: 11

Thr Gln Lys Pro Pro Ser Pro Pro Met Pro Ser Arg Gly Thr Leu Gly
1               5                   10                  15

Arg Asn Thr Pro Tyr Lys Thr Leu Glu Pro Val Lys Pro Pro Thr Val
            20                  25                  30

Pro Asn Asp Xaa Met Thr Ser Pro
        35                  40

<210> SEQ ID NO 12
<211> LENGTH: 40
<212> TYPE: PRT
<213> ORGANISM: Human
<220> FEATURE:
<221> NAME/KEY: MISC_FEATURE
<222> LOCATION: (36)..(36)
<223> OTHER INFORMATION: X is phosphotyrosine

<400> SEQUENCE: 12

Thr Gln Lys Pro Pro Ser Pro Pro Met Ser Gly Lys Gly Thr Leu Gly
1               5                   10                  15

Arg His Ser Pro Tyr Arg Thr Leu Glu Pro Val Arg Pro Pro Val Val
            20                  25                  30

Pro Asn Asp Xaa Val Pro Ser Pro
        35                  40

<210> SEQ ID NO 13
<211> LENGTH: 55
<212> TYPE: PRT
<213> ORGANISM: Drosophila melanogaster
<220> FEATURE:
<221> NAME/KEY: MISC_FEATURE
<222> LOCATION: (51)..(51)
<223> OTHER INFORMATION: X is phosphotyrosine

<400> SEQUENCE: 13

Thr Thr Lys Pro Pro Ser Pro Pro Gln Met Ser Arg Ala Gly Asn Thr
1               5                   10                  15

Gly Thr Leu Gly Lys Ser Val Ser Asn Thr Gly Thr Leu Gly Lys Ser
            20                  25                  30

Ser Arg Ser Tyr Arg Thr Pro Pro Val Val Asn Pro Pro Gln Val Pro
```

```
                    35                  40                  45

Ser His Xaa Ala Pro Ser Pro
    50                  55

<210> SEQ ID NO 14
<211> LENGTH: 20
<212> TYPE: PRT
<213> ORGANISM: Human
<220> FEATURE:
<221> NAME/KEY: MISC_FEATURE
<222> LOCATION: (14)..(14)
<223> OTHER INFORMATION: X is phosphotyrosine

<400> SEQUENCE: 14

Thr Leu Glu Pro Val Lys Pro Pro Thr Val Pro Asn Asp Xaa Met Thr
1               5                   10                  15

Ser Pro Ala Arg
            20

<210> SEQ ID NO 15
<211> LENGTH: 20
<212> TYPE: PRT
<213> ORGANISM: Artificial
<220> FEATURE:
<223> OTHER INFORMATION: Tryptic peptide pY213 F replacement

<400> SEQUENCE: 15

Thr Leu Glu Pro Val Lys Pro Pro Thr Val Pro Asn Asp Phe Met Thr
1               5                   10                  15

Ser Pro Ala Arg
            20

<210> SEQ ID NO 16
<211> LENGTH: 12
<212> TYPE: PRT
<213> ORGANISM: Artificial
<220> FEATURE:
<223> OTHER INFORMATION: Substrate peptide

<400> SEQUENCE: 16

Gly Gly Glu Ala Ile Tyr Ala Ala Pro Phe Lys Lys
1               5                   10

<210> SEQ ID NO 17
<211> LENGTH: 5
<212> TYPE: PRT
<213> ORGANISM: Artificial
<220> FEATURE:
<223> OTHER INFORMATION: Binding sequence

<400> SEQUENCE: 17

Pro Pro Ser Pro Pro
1               5

<210> SEQ ID NO 18
<211> LENGTH: 508
<212> TYPE: PRT
<213> ORGANISM: Homo sapiens

<400> SEQUENCE: 18

Met Ala Glu Leu Gln Met Leu Leu Glu Glu Ile Pro Ser Gly Lys
1               5                   10                  15

Arg Ala Leu Ile Glu Ser Tyr Gln Asn Leu Thr Arg Val Ala Asp Tyr
            20                  25                  30

Cys Glu Asn Asn Tyr Ile Gln Ala Thr Asp Lys Arg Lys Ala Leu Glu
```

```
            35                  40                  45
Glu Thr Lys Ala Tyr Thr Thr Gln Ser Leu Ala Ser Val Ala Tyr Gln
        50                  55                  60

Ile Asn Ala Leu Ala Asn Asn Val Leu Gln Leu Leu Asp Ile Gln Ala
 65                  70                  75                  80

Ser Gln Leu Arg Arg Met Glu Ser Ser Ile Asn His Ile Ser Gln Thr
                85                  90                  95

Val Asp Ile His Lys Glu Lys Val Ala Arg Arg Glu Ile Gly Ile Leu
            100                 105                 110

Thr Thr Asn Lys Asn Thr Ser Arg Thr His Lys Ile Ile Ala Pro Ala
        115                 120                 125

Asn Met Glu Arg Pro Val Arg Tyr Ile Arg Lys Pro Ile Asp Tyr Thr
    130                 135                 140

Val Leu Asp Asp Val Gly His Gly Val Lys Trp Leu Lys Ala Lys His
145                 150                 155                 160

Gly Asn Asn Gln Pro Ala Arg Thr Gly Thr Leu Ser Arg Thr Asn Pro
                165                 170                 175

Leu Thr Gln Lys Pro Pro Ser Pro Pro Met Ser Gly Arg Gly Thr Leu
            180                 185                 190

Gly Arg Asn Thr Pro Tyr Lys Thr Leu Glu Pro Val Lys Pro Pro Thr
        195                 200                 205

Val Pro Asn Asp Tyr Met Thr Ser Pro Ala Arg Leu Gly Ser Gln His
    210                 215                 220

Ser Pro Gly Arg Thr Ala Ser Leu Asn Gln Arg Pro Arg Thr His Ser
225                 230                 235                 240

Gly Ser Ser Gly Gly Ser Gly Ser Arg Glu Asn Ser Gly Ser Ser Ser
                245                 250                 255

Ile Gly Ile Pro Ile Ala Val Pro Thr Pro Ser Pro Thr Ile Gly
            260                 265                 270

Pro Glu Asn Ile Ser Val Pro Pro Ser Gly Ala Pro Pro Ala Pro
        275                 280                 285

Pro Leu Ala Pro Leu Leu Pro Val Ser Thr Val Ile Ala Ala Pro Gly
    290                 295                 300

Ser Ala Pro Gly Ser Gln Tyr Gly Thr Met Thr Arg Gln Ile Ser Arg
305                 310                 315                 320

His Asn Ser Thr Thr Ser Ser Thr Ser Ser Gly Gly Tyr Arg Arg Thr
                325                 330                 335

Pro Ser Val Thr Ala Gln Phe Ser Ala Gln Pro His Val Asn Gly Gly
            340                 345                 350

Pro Leu Tyr Ser Gln Asn Ser Ile Ser Ile Ala Pro Pro Pro Pro
        355                 360                 365

Met Pro Gln Leu Thr Pro Gln Ile Pro Leu Thr Gly Phe Val Ala Arg
    370                 375                 380

Val Gln Glu Asn Ile Ala Asp Ser Pro Thr Pro Pro Pro Pro Pro
385                 390                 395                 400

Pro Asp Asp Ile Pro Met Phe Asp Asp Phe Pro Pro Pro Pro Pro
                405                 410                 415

Pro Pro Val Asp Tyr Glu Asp Glu Glu Ala Ala Val Val Gln Tyr Asn
            420                 425                 430

Asp Pro Tyr Ala Asp Gly Asp Pro Ala Trp Ala Pro Lys Asn Tyr Ile
        435                 440                 445

Glu Lys Val Val Ala Ile Tyr Asp Tyr Thr Lys Asp Lys Asp Asp Glu
    450                 455                 460
```

-continued

| | | | | | | | | | | | | | | |
|---|---|---|---|---|---|---|---|---|---|---|---|---|---|---|
| Leu | Ser | Phe | Met | Glu | Gly | Ala | Ile | Ile | Tyr | Val | Ile | Lys | Lys | Asn | Asp |
| 465 | | | | 470 | | | | | 475 | | | | | | 480 |
| Asp | Gly | Trp | Tyr | Glu | Gly | Val | Cys | Asn | Arg | Val | Thr | Gly | Leu | Phe | Pro |
| | | | | 485 | | | | | 490 | | | | | 495 | |
| Gly | Asn | Tyr | Val | Glu | Ser | Ile | Met | His | Tyr | Thr | Asp | | | | |
| | | | 500 | | | | | 505 | | | | | | | |